US009476102B2

(12) United States Patent
Bau et al.

(10) Patent No.: US 9,476,102 B2
(45) Date of Patent: Oct. 25, 2016

(54) ISOTHERMAL NUCLEIC ACID AMPLIFICATION REACTOR WITH INTEGRATED SOLID STATE MEMBRANE

(75) Inventors: Haim H. Bau, Swarthmore, PA (US); William R. Abrams, Merion, PA (US); Eran Geva, Brooklyn, NY (US); Michael G. Mauk, Greenville, DE (US); Changchun Liu, Bala Cynwyd, PA (US); Daneil Malamud, New York, NY (US); Xianbo Ceiu, Beijing (CN)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 328 days.

(21) Appl. No.: 14/001,347

(22) PCT Filed: Feb. 15, 2012

(86) PCT No.: PCT/US2012/025196
§ 371 (c)(1),
(2), (4) Date: Nov. 4, 2013

(87) PCT Pub. No.: WO2013/103360
PCT Pub. Date: Jul. 11, 2013

(65) Prior Publication Data
US 2014/0162244 A1 Jun. 12, 2014

Related U.S. Application Data

(60) Provisional application No. 61/446,850, filed on Feb. 25, 2011.

(51) Int. Cl.
| C12Q 1/70 | (2006.01) |
| C12M 1/00 | (2006.01) |
| C12Q 1/68 | (2006.01) |
| B01L 3/00 | (2006.01) |

(52) U.S. Cl.
CPC ............ *C12Q 1/703* (2013.01); *B01L 3/5023* (2013.01); *B01L 3/502738* (2013.01); *C12Q 1/6806* (2013.01); *C12Q 1/6844* (2013.01); *B01L 3/502715* (2013.01); *B01L 2200/026* (2013.01); *B01L 2200/10* (2013.01); *B01L 2300/0681* (2013.01); *B01L 2300/087* (2013.01); *B01L 2300/0816* (2013.01); *B01L 2300/0867* (2013.01); *B01L 2300/1827* (2013.01); *B01L 2300/1861* (2013.01); *B01L 2400/0406* (2013.01); *B01L 2400/065* (2013.01); *B01L 2400/0644* (2013.01)

(58) Field of Classification Search
None
See application file for complete search history.

(56) References Cited

U.S. PATENT DOCUMENTS

| 5,984,257 | A | 11/1999 | Baek et al. | |
| 2001/0036634 | A1 | 11/2001 | Chow et al. | |
| 2004/0110167 | A1* | 6/2004 | Gerdes | C12Q 1/6834 435/6.11 |
| 2009/0186357 | A1 | 7/2009 | Mauk et al. | |
| 2010/0035349 | A1 | 2/2010 | Bau et al. | |

FOREIGN PATENT DOCUMENTS

WO WO 2013/103360 7/2013

OTHER PUBLICATIONS

U.S. Appl. No. 61/488,823, filed May 23, 2011, Bau.
Bau,H.H," Molecular Diagnostics at the Point of Testing", Cancer Detection and Diagnostics Technologies for Global Health, National Cancer Institute, Aug. 22-23, 2011, NIH Campus, Rockville, Maryland, pp. 27-28.
Branson, B. M., "Point-of-Care Rapid Tests for HIV Antibodies Antibodies/Patientennahe Schnelltests für den Nachweis von HIV-Antikörpern", J. Lab. Med. Aug. 2003,27(7/8), 288-295.
Butler, S. L., "A Quantitative Assay for HIV DNA Integration In Vivo", Nature Medicine, May 2001, 7(5), 631-634.
Chen, D., "An Integrated, Self-Contained Microfluidic Cassette for Isolation, Amplification, and Detection of Nucleic Acids", Biomed., Microdevices, Aug. 2010, 12(4), 705-719.
Chen, Z., "A Microfluidic System for Saliva-Based Detection of Infectious Diseases", Ann. NY Acad. Sci., Mar. 2007, 1098, 429-436.
Cheng, X., "Enhancing the Performance of a Point-Of-Care CD4+ T-cell Counting Microchip Through Monocyte Depletion for HIV/AIDS Diagnostics", Lab Chip, May 2009, 9(10), 1357-1364, Published Online Feb. 4, 2009.
Curtis, K. A, Sequence-Specific Detection Method for Reverse Transcription, Loop-Mediated Isothermal Amplification of HIV-1, J. Med. Viral., 2009, 81(6), 966-972.
Curtis, K. A., "Rapid Detection of HIV-1 by Reverse-Transcription, Loop-Mediated Isothermal Amplification (RT-LAMP)", J. Viral. Meth., Aug. 2008, 151(2), 264-270.
Dimov, I. K., "Integrated microfluidic tmRNA purification and real-time NASBA device for molecular diagnostics", Lab Chip, Oct. 2008, 8, 2071-2078.
Dineva, M.A., "Sample Preparation: A Challenge in the Development of Point-Of-Care Nucleic Acid-Based Assays for Resource-Limited Settings", Analyst, 2007, 132, 1193-1199, Published online Oct. 1, 2007.
Donovan, et al, "HIV infection: Point-Of-Care Testing", Annuals of Pharmacotherapy, Apr. 2004, 38(4), 670-676.
Easley, C. J., "A Fully Integrated Microfluidic Genetic Analysis System With Sample-In-Answer-Out Capability", Proc. Natl. Acad. Sci. USA., Dec. 19, 2006, 103(51), 19272-19277.
Fang, X., Loop-Mediated Isothermal Amplification Integrated on Microfluidic Chips for Point-of-Care Quantitative Detection of Pathogens, Anal. Chem., Apr. 1, 2010, 82(7), 3002-3006.

(Continued)

*Primary Examiner* — David Thomas
(74) *Attorney, Agent, or Firm* — Baker & Hostetler LLP

(57) ABSTRACT

Provided are devices adapted to isolate, amplify, and detect nucleic acids that may be present in a biological sample. The devices can, in some embodiments, isolate, amplify, and detect nucleic acid in a single chamber. In other embodiments, the devices are adapted to isolate and amplify nucleic acids in a reaction chamber, after which the nucleic acids may be communicated to a pervious medium—such as a lateral flow strip—where the user may label and detect the nucleic acids.

23 Claims, 21 Drawing Sheets

(56) References Cited

OTHER PUBLICATIONS

Gibellini, et al, "Quantitative Detection of Human Immunodeficiency Virus Type 1 (HIV-1) Viral Load by SYBR Green Real-Time RT-PCR Technique in HIV-1 Seropositive Patients", J. Viral. Meth., Feb. 2004, 115(2), 183-189.
Herr, A. E., Microfluidic Immunoassays As Rapid Saliva-Based Clinical Diagnostics, Proc. Natl. Acad. Sci. USA, Mar. 27, 2007, 104(13), 5268-5273.
Hill, et al, "Loop-Mediated Isothermal Ampli-Cation Assay for Rapid Detection of Common Strains of *Escherichia coli*", J. Clin. Microbial., Jun. 2008, 46(8), 2800-2804.
International Patent Application No. PCT/US2012/025196: International Search Report and the Written Opinion dated May 29, 2012, 10 pages.
Jokerst, et al, "Integration of Semiconductor Quantum Dots Into Nano-Bio-Chip Systems for Enumeration of CD4+ T Cell Counts At the Point-Of-Need", Lab Chip, Dec. 2008, 8(12), 2079-2090.
Kibbe, W.A., "Oligo Calc: An Online Oligonucleotide Properties Calculator", Nucleic Acids Research, 2007, 35, Web Server issue W43-W46, Published online Apr. 22, 2007. www.basic.northwestern.edu/biotools/oligocalc.html.
Kim, J., "A Disposable, Self-Contained PCR Chip", Lab Chip, Feb. 21, 2009, 9(4), 606-612.
Kim, J., "A PCR Reactor With an Integrated Alumina Membrane for Nucleic Acid Isolation", Analyst, 2010, 135, 2408-2414.
Lagally, E. T., "Fully Integrated Pcr-Capillary Electrophoresis Microsystem for DNA Analysis", Lab Chip, Nov. 2001, 1, 102-107.
Lee, S. H., "A Polymer Lab-On-A-Chip for Reverse Transcription (RT)-PCR Based Point-Of-Care Clinical Diagnostics", Lab Chip, Dec. 2008, 8(12), 2121-2127.
Lee, C. S., "Multiplex PCR for the Simultaneous Detection of Pseudorabies Virus, Porcine Cytomegalovirus, and Porcine Circovirus in Pigs", J. Viral. Methods, Jan. 2007, 139(1), 39-43.
Lee, J., "Microchip-based one step DNA extraction and real-time PCR in one chamber for rapid pathogen identification", Lab Chip, May 2006, 6(7), 886-895.
Legendre, L.A., "A Simple, Valveless Microfluidic Sample Preparation Device for Extraction and Amplification of DNA From Nanoliter-Volume Samples", Anal. Chem., 2006, 78, 1444-1451.
Liu et al, "An Isothermal Amplification Reactor With an Integrated Isolation Membrane for Point-Of-Care Detection of Infectious Diseases", Analyst, May 21, 2011, 136(10), 2069.
Liu, C., "A Timer-Actuated Immunoassay Cassette for Detecting Molecular Markers in Oral Fluids", Lab Chip, Mar. 21, 2009, 9(6), 768-776, Published online on Dec. 5, 2008.
Liu, R. H., "Self-Contained, Fully Integrated Biochip for Sample Preparation, Polymerase Chain Reaction Amplification, and DNA Microarray Detection", Anal. Chem., Apr. 1, 2004, 76(7), 1824-1831.
Liu, "A Disposable, Integrated Loop-Mediated Isothermal Amplification Cassette With Thermally Actuated Valves", Microfluidics and Nanofluidics, Aug. 2011, 11(2), 209-220.
Liu et al, "Self Heating Cassette for Point of Care Molecular Diagnostics", Lab on Chip, 10.1039.
Malamud, "Point Detection of Pathogens in Oral Samples", Adv. Dent. Res., Jun. 2005, 18(1),12-16.
Malamud, D., "Oral Diagnostic Testing for Detecting Human Immunodeficiency Virus-1 Antibodies: A Technology Whose Time Has Come", Am. J Med., Apr. 1, 1997, 102(4A), 9-14.
Malamud, D., "Saliva As a Diagnostic Fluid", Br. Med. J, Jul. 25, 1992, 305(6847), 207-208.
Malnati, M.S., A Universal Real-Time PCR Assay for the Quantification of Group-M HIV-1 Proviral Load.Nature Protocols, 2008, 3(7), 1240-1248, Published online Jul. 3, 2008.
Mehta, N., "Low-Cost HIV-1 Diagnosis and Quantification in Dried Blood Spots by Real Time PCR", PLoS One, Jun. 5, 2009,4(6), e5819.
Notomi, et al, "Loop-Mediated Isothermal Amplification of DNA", Nucleic Acids Res., Jun. 15, 2000, 28(12), E63.
Ochert, A. S., "Inhibitory Effect of Salivary Fluids on PCR: Potency and Removal", Genome Res., 1994, 3, 365-368.
Owen et al, "Alternative algorithms for human immunodeficiency virus infection diagnosis using tests that are licensed in the United States", J. Clin. Microbiol, May 2008, 46(5), 1588-1595.
Palmer, S., "New Real-Time Reverse Transcriptase-Initiated PCR Assay with Single-Copy Sensitivity for Human Immunodeficiency Virus Type 1 RNA in Plasma", J. Clin. Microbial., Oct. 2003, 41(10), 4531-4536.
Rouet, F., "Transfer and Evaluation of an Automated, Low-Cost Real-Time Reverse Transcription-PCR Test for Diagnosis and Monitoring of Human Immunodeficiency Virus Type 1 Infection in a West African Resource-Limited Setting", J. Clin. Microbial. Jun. 2005, 43(8), 2709-2717.
Saha, B. K., "Quantitation of HIV-1 by Real-Time PCR With a Unique Fluorogenic Probe", J. Viral. Methods, Apr. 2001, 93(1-2), 33-42.
Segal, A., "Salivary Diagnostics: Enhancing Disease Detection and Making Medicine Better", Eur. J Dent. Educ., Feb. 2008, 12(Suppl 1), 22-29.
Shen, F., "Nanoliter Multiplex PCR arrays on a SlipChip", Anal. Chem., Jun. 1, 2010, 82(11),4606-4612.
Thai et al, "Development and Evaluation of a Novel Loop-Mediated Isothermal Amplification Method for Rapid Detection of Severe Acute Respiratory Syndrome Coronavirus", J. Clin. Microbial., 2004, 42(5),1956-1961.
Tomita, N., "Loop-Mediated Isothermal Amplification (LAMP) of Gene Sequences and Simple Visual Detection of Products", Nature Protocols, 2009, 3(5), 877-882, Published online Apr. 24, 2008.
Wang, J., "A Disposable Microfluidic Cassette for DNA Amplification and Detection", Lab Chip Jan. 1, 2006, 6(1), 46-53.
Westh, H., "Multiplex Real-Time PCR and Blood Culture for Identification of Bloodstream Pathogens in Patients With Suspected Sepsis", Clin. Microbial. Infect., Jun. 2009, 15(6), 544-551.
Yager, P., "Microfluidic Diagnostic Technologies for Global Public Health", Nature, Jul. 27, 2006, 442(7101), 412-418.
Ziober, B. L., "Lab-On-A-Chip for Oral Cancer Screening and Diagnosis", Head Neck, Jan. 2008, 30, 111-121.

* cited by examiner

ISOTHERMAL NUCLEIC ACID AMPLIFICATION REACTOR WITH INTEGRATED SOLID STATE MEMBRANE

CROSS-REFERENCE TO RELATED APPLICATIONS

This application is the National Stage of International Application No. PCT/US2012/025196, filed Feb. 15, 2012, which claims the benefit of U.S. Provisional Application No. 61/446,850, filed Feb. 25, 2011, the entireties of which applications are incorporated herein by reference in their entireties for any and all purposes.

GOVERNMENT RIGHTS

This invention was supported by the National Institutes of Health and the National Institute of Dental and Craniofacial Research (grant no. U01DE017855). The government has certain rights in this invention.

TECHNICAL FIELD

The present invention relates to the fields of microfluidic devices and to the field of nucleic acid amplification.

BACKGROUND

In recent years, there has been a growing interest in point of care testing (PoCT) to provide health care personnel with timely information that facilitates informed decisions; to monitor spread of diseases and contaminants; and to make sophisticated capabilities available outside centralized laboratories such as in poor resource regions.

Despite global efforts to control the acquired immune deficiency syndrome (AIDS) pandemic, the human immunodeficiency virus (HIV) infection continues to spread relatively unabated in many parts of the world. The diagnosis of HIV infection at the point-of-care and in resource-poor settings poses considerable challenges due to the time delay between sample collection and diagnosis. The lack of a rapid, confirmed diagnosis leaves many individuals unaware of their condition and impedes tracking of patients by health providers.

To date, most efforts in this field have focused on detecting pathogens and antibodies in blood or plasma. In many cases, oral fluids contain the same pathogens and proteins as blood, but often at lower concentrations. Oral fluids, however, can be collected non-invasively by individuals with little training and without a need for special equipment. In addition, it may be is easier to collect oral fluid samples from children and the elderly than blood samples, collection of oral fluids is subject to fewer regulations compared with the collection of blood, and oral fluid collection reduces the risk of infection to the health care worker who collects the sample. However, since the oral fluid is a complex mixture of saliva secreted by parotid and other salivary glands, gingival cervicular fluid from the gingival crevice, and secretions from the mucous membranes, amplification of nucleic acids in oral fluid is challenging.

Accordingly, there is a need in the field for integrated diagnostic devices capable of performing nucleic acid testing at the point-of-care for detection of various disorders and diseases, including HIV.

SUMMARY

In addressing the described challenges, disclosed herein are microfluidic cassettes that in some embodiments integrate nucleic acid capture, concentration, and purification; isothermal amplification; and real-time fluorescence detection into one chamber. One embodiment includes a membrane (e.g., from Flinders Technology Associates, Whatman FTA™) in the amplification chamber. The membrane may be as a filter, which allows one to accommodate comparatively large sample volumes and detect low-concentration targets.

In addition to facilitating isolation and concentration of nucleic acids, the membrane may remove amplification inhibitors from oral fluids, which may reduce amplification efficiency. To simplify cassette operation, the extracted nucleic acid may be amplified in the isolation chamber without a separate step for the elution of the immobilized nucleic acids. The amplification process may be monitored in real time with a compact, portable fluorescence reader. The utility of this integrated cassette was demonstrated by detecting HIV in oral fluids with a sensitivity of 10 HIV virus particles per sample.

In a first aspect, the present disclosure provides analysis devices, comprising a chamber; a capture material that preferentially binds nucleic acids, the capture material being positioned such that the capture material is capable of fluid communication with the interior of the reaction chamber; and a first pervious body adapted to be movably positionable such that the first pervious body is in fluid communication with the reaction chamber.

Also provided are devices, the devices including a chamber; and a capture material that preferentially binds nucleic acids, the capture material being positioned such that the capture material is capable of fluid communication with the interior of the reaction chamber.

Further provided are methods, the methods suitably comprising isolating a nucleic acid on a capture material that preferentially binds nucleic acids, the capture material being disposed within a chamber; amplifying, in the chamber, at least a portion of the one or more of the nucleic acids by loop-mediated amplification to give rise to an amplification product comprising one or more amplified nucleic acids; transferring, by capillary action, the amplification product to a pervious medium; and detecting the presence of the amplification product on the pervious medium.

Also provided are methods, comprising isolating a nucleic acid on a capture material that preferentially binds nucleic acids, the capture material being disposed within a chamber; amplifying, in the chamber, at least a portion of the one or more of the nucleic acids by loop-mediated amplification to give rise to an amplification product comprising one or more amplified nucleic acids; and detecting the presence of the amplification product within the chamber.

BRIEF DESCRIPTION OF THE DRAWINGS

The summary, as well as the following detailed description, is further understood when read in conjunction with the appended drawings. For the purpose of illustrating the disclosure, there are shown in the drawings exemplary embodiments of the disclosure; however, the disclosure is not limited to the specific methods, compositions, and devices disclosed. In addition, the drawings are not necessarily drawn to scale. In the drawings:

FIG. 2A depicts a single-chamber, microfluidic cassette with an integrated FTA™ membrane and cassette holder equipped with a thin film heater, a thermocouple, and a seat for the detector. The fluorescent signal is excited and detected with a portable, compact, ESE optical detector shown in FIG. 2B. The cassette in FIG. 2A is located in its working position. FIG. 2C depicts an optical reader is inserted in the cassette holder. The cassette is being placed into its working position under the detector. A design (such as the design shown in FIG. 2A) where the cassette is inserted into a heating block upon which is mounted a commercial fluorescent reader provides ease of use. The thermal contact between the cassette and heater is not as critical with isothermal amplification, so a simple insertion method works well. (This is not the case with PCR where a good thermal conduct between the chip and heating/cooling element is crucial for efficient thermal cycling. Also the long inlet and outlet channels extend out into the unheated areas of the chip. Unlike PCR systems, this chip can be operated without sealing the amplification chamber, which simplifies operation.

FIG. 8A depicts the processor for real-time amplification and detection with electrical heating. The cassette holder is equipped with a thin film resistance heater, a thermocouple, and a seat for the detector. In FIG. 8B, the fluorescent signal is excited and detected with a portable, compact (match-box size, Qiagen ESE Fluo Sens SD 003) optical reader. Other readers (e.g., an LED and a cellphone camera may be used (see FIG. 8D)). FIG. 8C depicts a cassette heated with a self-regulating exothermic reaction chamber (no electrical power is required). The amplification reactor is maintained at 60-65° C. independent of the ambient temperatures. FIG. 8D demonstrates the feasibility of monitoring fluorescent emission with a cell phone camera. The devices in FIG. 8C and 8D feature two reactors, but can contain an array of amplification reactors for concurrent detection of multiple pathogens and for control, calibration, and quantification.

DETAILED DESCRIPTION OF ILLUSTRATIVE EMBODIMENTS

Figure 1:
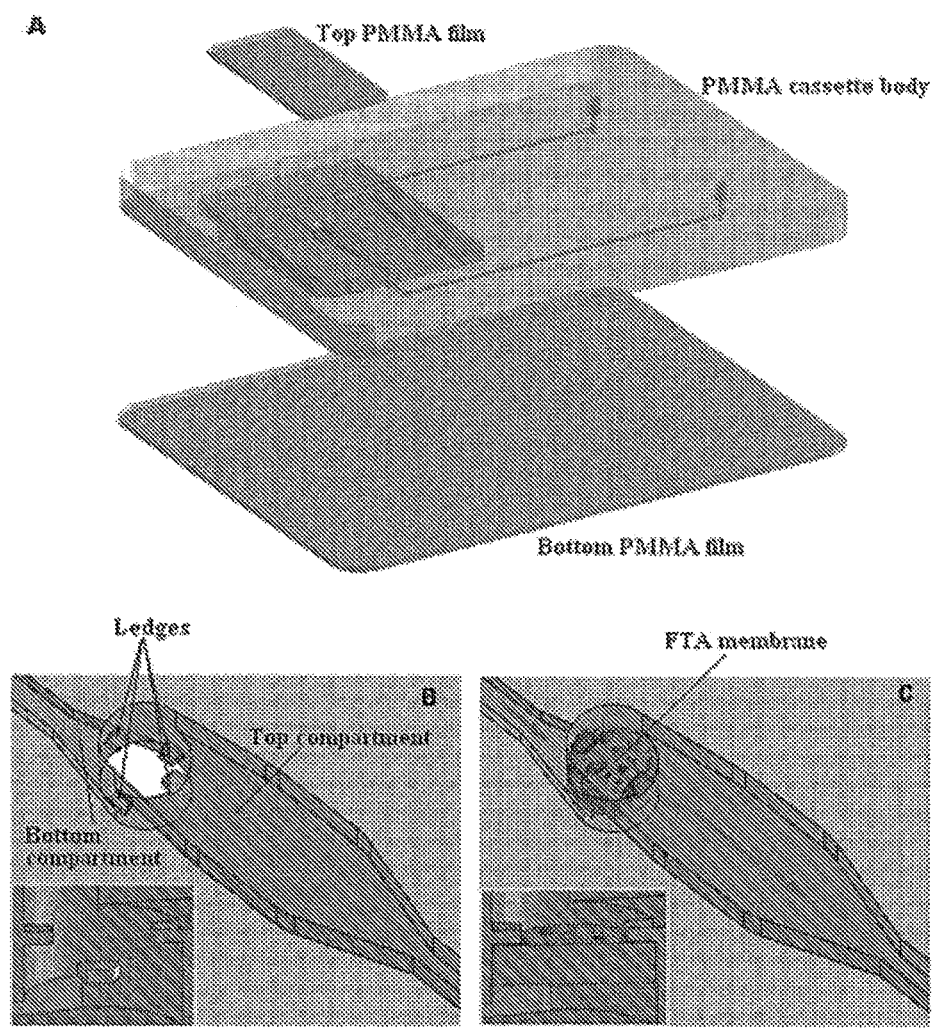
FIG. 1 illustrates an exemplary integrated cassette. (A) Exploded view. The cassette consists of three solvent-bonded layers of PMMA. The cassette's features were milled in the main body of the cassette. (B) An amplified view of the reaction chamber without the FTA™ membrane. Two sets of protruding ledges were machined on the top and bottom of the LAMP chamber. (C) An amplified view of the reaction chamber with the installed FTA™ membrane, which separates the reaction chamber into a top main compartment and a bottom compartment.

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claims. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Any documents cited herein are incorporated herein by reference in their entireties for any and all purposes.

A simple, point of care, inexpensive, disposable cassette for the detection of nucleic acids extracted from pathogens was designed, constructed, and tested. The cassette utilizes a single reaction chamber for isothermal amplification of nucleic acids. The chamber may be equipped with an integrated, flow-through, Flinders Technology Associates (Whatman FTA™) membrane for the isolation, concentration, and purification of DNA and/or RNA; other nucleic acid capture materials are also suitable. The nucleic acids captured by the membrane are used directly as templates for amplification without elution, thus simplifying the cassette's flow control. The FTA™ membrane also serves another role—removal of inhibitors that dramatically reduce detection sensitivity. Thermal control is provided with a thin film heater external to the cassette. The amplification process was monitored in real time with a portable, compact fluorescent reader. The utility of the integrated, single-chamber cassette was demonstrated by detecting the presence of HIV-1 in oral fluids. The HIV RNA was reverse transcribed and subjected to loop-mediated, isothermal amplification (LAMP). A detection limit of less than 10 HIV particles was demonstrated. The cassette is particularly suitable for resource poor regions, where funds and trained personnel are in short supply. The cassette can be readily modified to detect nucleic acids associated with other pathogens borne in saliva, urine, and other body fluids as well as in water and food.

In a first embodiment, the present disclosure provides analysis devices. The devices suitably include a chamber; a capture material that preferentially binds nucleic acids, the capture material being positioned such that the capture material is capable of fluid communication with the interior of the reaction chamber; and a first pervious body adapted to be movably positionable such that the first pervious body is in fluid communication with the reaction chamber. By pervious is meant a material that is permeable to fluid, such as a porous or fibrous material. The chamber may be polymeric or metallic in material, and may suitably have a volume of from about 0.01 microliters to about 10 or even about 50 milliliters.

As described elsewhere herein, the capture material may be an FTA™ membrane. Silica is a material that preferentially bind nucleic acid. The first pervious body is suitably adapted to be movably positionable such that the first pervious body contacts the capture material. The body may be in the form of a strip, such as the absorbent sinkpad shown in FIG. 11. The first pervious body may act to remove fluid disposed within the chamber when the pervious body is contacted to a membrane or other material disposed at the outlet of the chamber. The fluid removal may be accomplished by wicking or capillary action. The first pervious body may, as shown, be movable between two or more positions, suitably including a position that allows the body to take up fluid from within the chamber.

Figure 10:
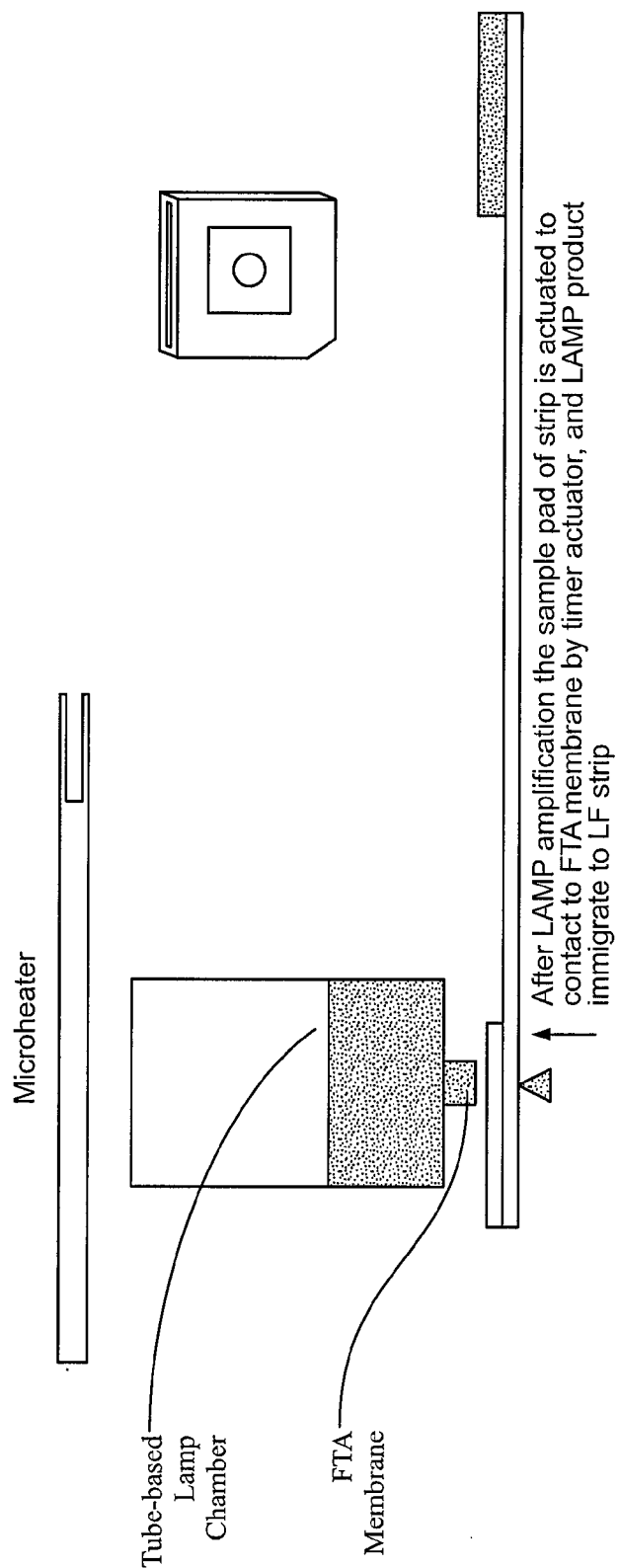
FIG. 10 illustrates a cutaway view of an exemplary LAMP chamber, with a lateral flow strip configured to contact the membrane.
Figure 11:
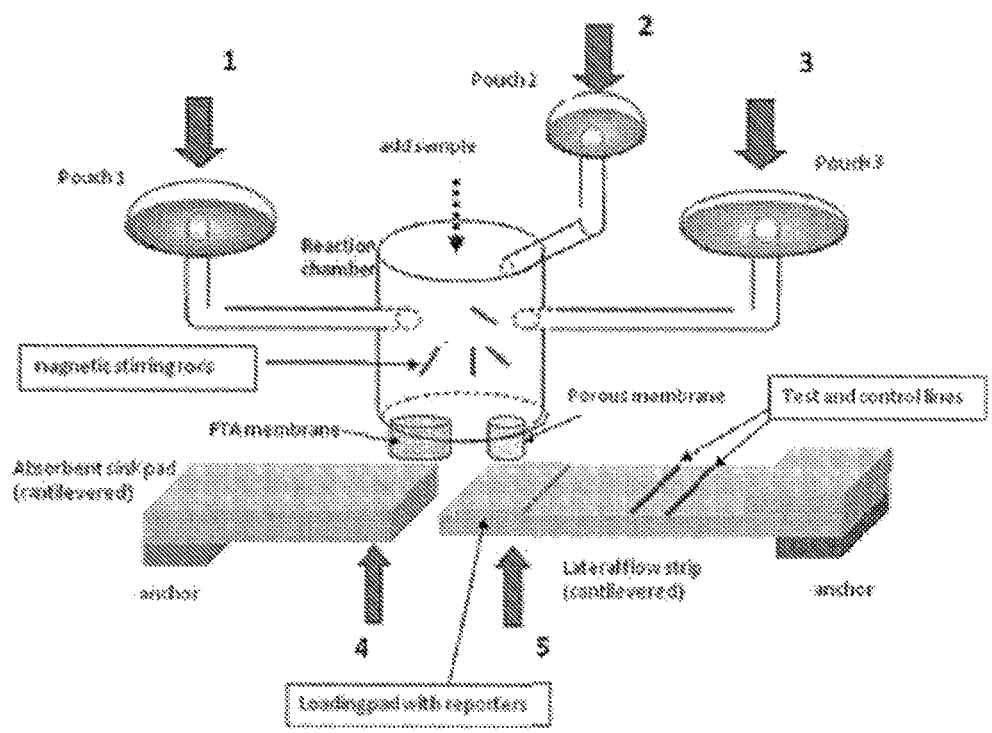
FIG. 11 illustrates an exemplary embodiment of the disclosed devices.

The capture material may, as shown in FIG. 10 and FIG. 11, be positioned at an outlet of the chamber. The capture material is suitably seated at the outlet, so as to stabilize the location of the capture material.

The devices may also include a transport material disposed at an outlet of the chamber, the transport material being pervious. The transport material may be a porous membrane (e.g., cellulose or other porous material) that is disposed at an outlet of the chamber, as illustrated in FIG. 11 by the porous membrane disposed at an outlet of the chamber. The transport material is suitably a material that is non-reactive with biological samples, although this is not a requirement. A device may also include a second pervious body, the second pervious body being movably positionable such that the second pervious body contacts the transport material. In this way, sample disposed within the chamber is drawn out of the chamber when the second pervious body (e.g., lateral flow strip) contacts a porous material disposed at an outlet of the chamber. Such a pervious body is shown by the cantilevered lateral flow strip in FIG. 11. The second pervious body be moveable such that it may be moveable between a position that allows the flow strip to take up fluid from within the chamber.

In some embodiments, the second pervious body includes a binding moiety adapted to bind to a nucleic acid communicated from the transport material to the second pervious body. The binding moiety may be, for example, an antibody, an antigen, a receptor, a ligand, a nucleic acid, and the like. The second pervious body may also include a reporter molecule adapted to associate with a nucleic acid communicated from the transport material to the second pervious body. The reporter molecule may be a tag, such as a dye or label that enables a user to detect (e.g., by visualizing) the presence of a labeled sample nucleic acid.

In some embodiments, the second pervious body includes a region that is adapted to bind to a binding moiety that is itself bound to a sample. For example, the pervious body may include a region that binds to a particular antibody, which antibody is in turn bound to a nucleic acid that exits the reactor chamber. The nucleic acid may also be labeled, and the user may then detect the presence (or absence) of labeled nucleic acids on the second pervious body. The pervious body may include a test and a control region.

The devices may include one or more quantities of fluid stored such that the fluid may be introduced to the interior of the chamber. The fluid may be stored in a pouch, baggie, or other container that may be pierced, squeezed, or otherwise opened so as to liberate the container's contents. Suitable fluids include buffers, lysing agents, nucleic acid amplification agents (including primers and enzymes), water, acids, bases, and the like.

The disclosed devices may also include a device adapted to heat the chamber. The heater may be a wire heater, a thin film heater, a radiant heater, and the like—virtually any heater may be used. The heater may include a controller so as to allow the user to set or even maintain a particular temperature or temperature schedule. The heater may be exterior to the chamber, although it may also be incorporated into the chamber or even reside at least partially within the chamber.

A user may also include a detector capable of detecting the presence of one or more nucleic acids disposed on the second pervious body. The detector may be an image capture device (such as a camera, CCD, fluorometer, and the like).

Figure 13:
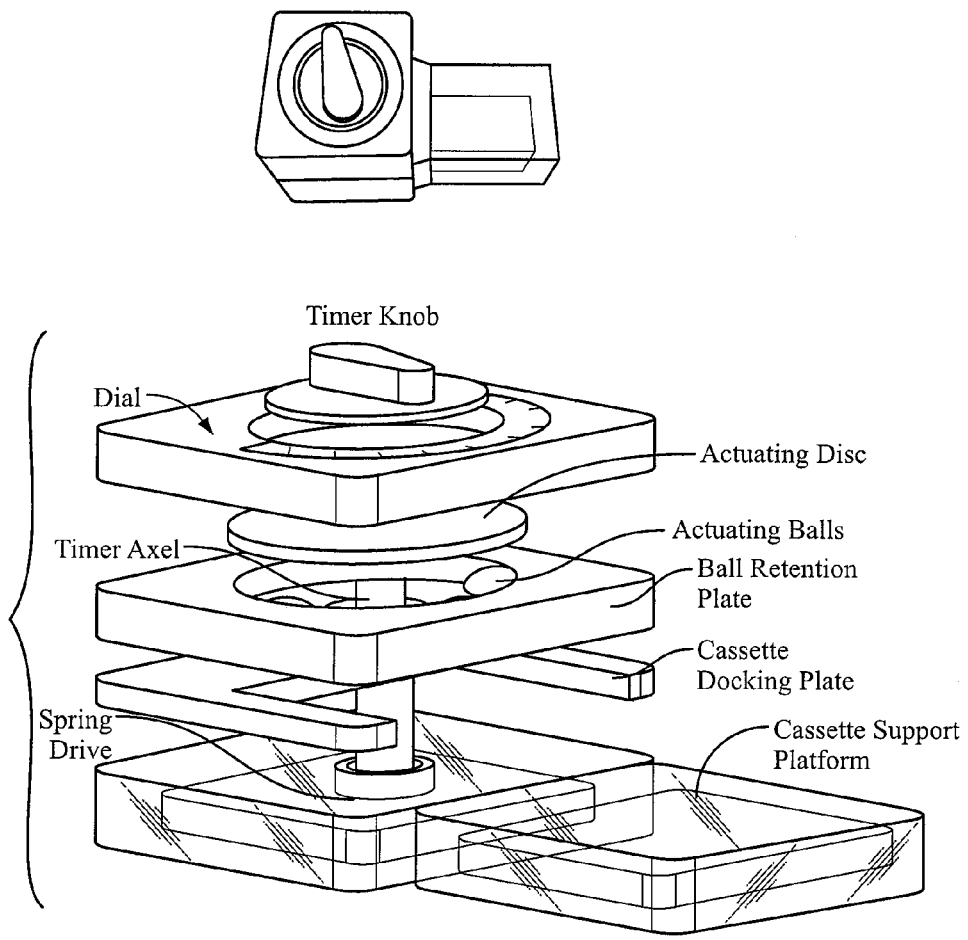
FIG. 13 illustrates an exemplary timer-actuated device.
Figure 14:
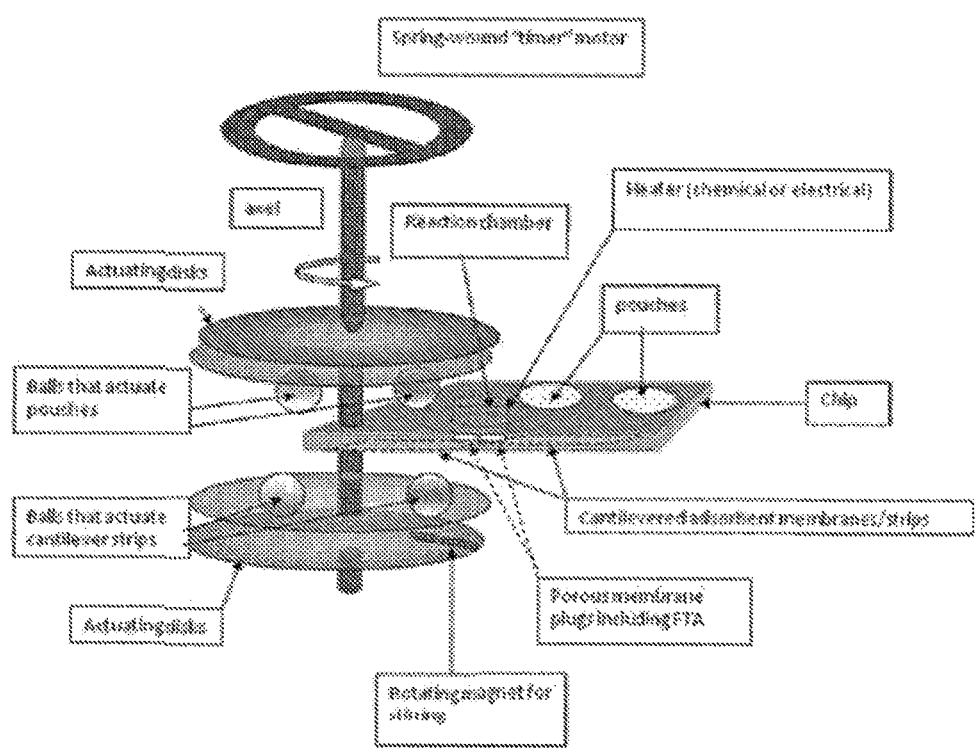
FIG. 14 illustrates an exemplary device according to the present disclosure that includes cantilevered membranes.
Figure 15:
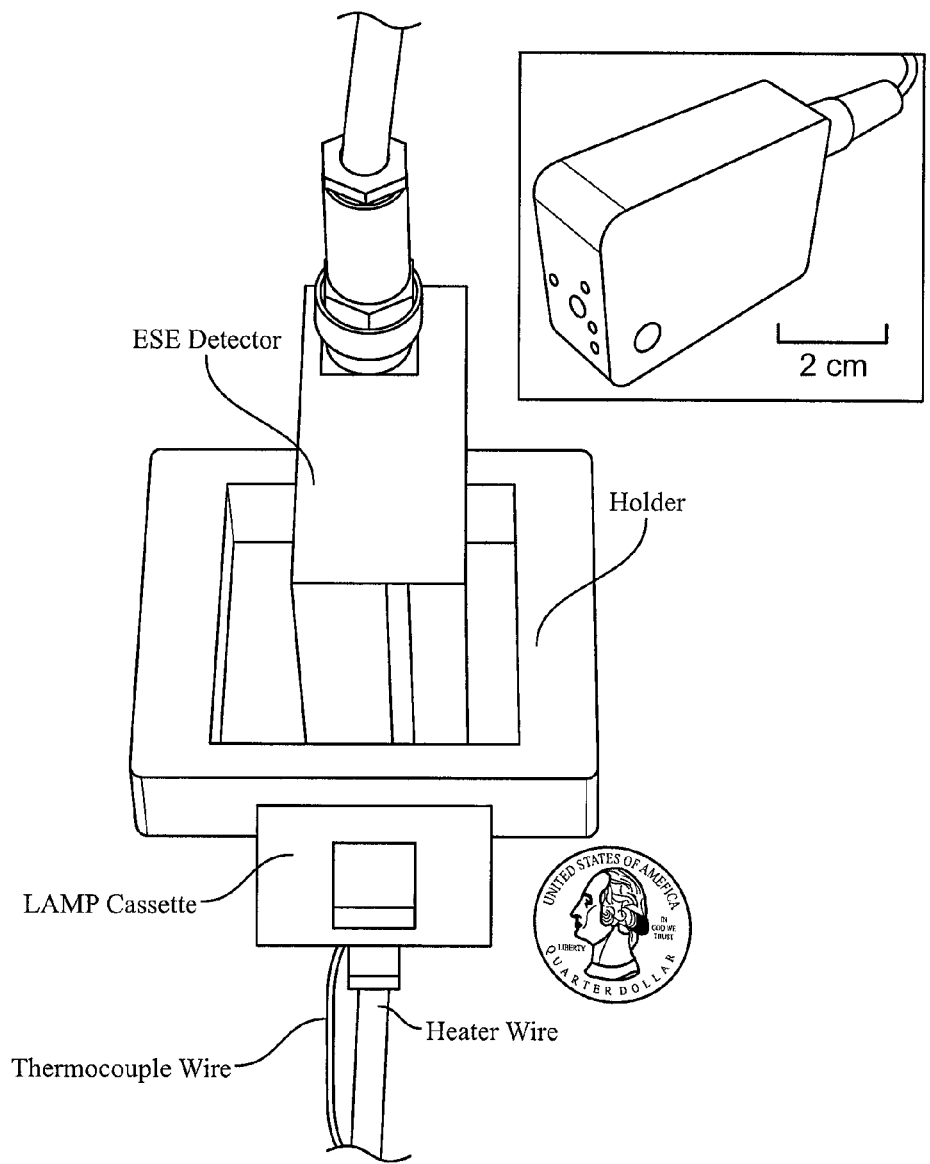
FIG. 15 illustrates an exemplary LAMP device with detector.
Figure 16:
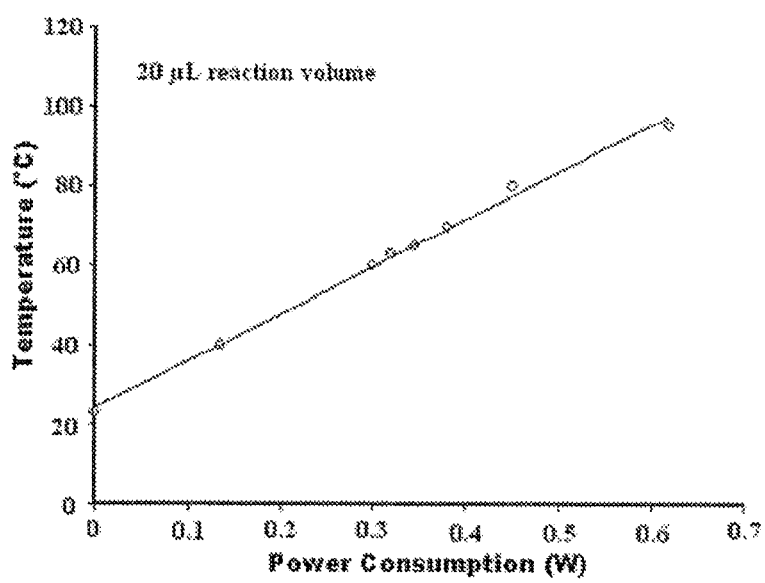
FIG. 16 illustrates electrical power consumption to heat a 20 microliter LAMP reaction.

A user may also incorporate a device configured to modulate delivery of fluid into the reaction chamber. As shown in FIG. 13 and FIG. 14, such a device may be a timer-actuated device that actuates pouches or other components of the devices according to a preset schedule. The device may include one or more projections that contact or otherwise actuate fluid containers or even switches or other controls that modulate the movement or even temperature of the various device components. The device may also be computer controlled, in which case a computer actuates one or more components of the device. For example, the computer may modulate the delivery of sample into the chamber, followed by modulating the delivery of fluid into the chamber so as to liberate and then isolate nucleic acid on the capture material, followed by modulating the removal of liberated nucleic acid from the chamber for detection. A device that modulates fluid delivery may be one that rotates, translates, or both, so as to actuate the container according to a preprogrammed schedule. Such a device may include a device having a rotating disk that features one or more projections.

Figure 17:
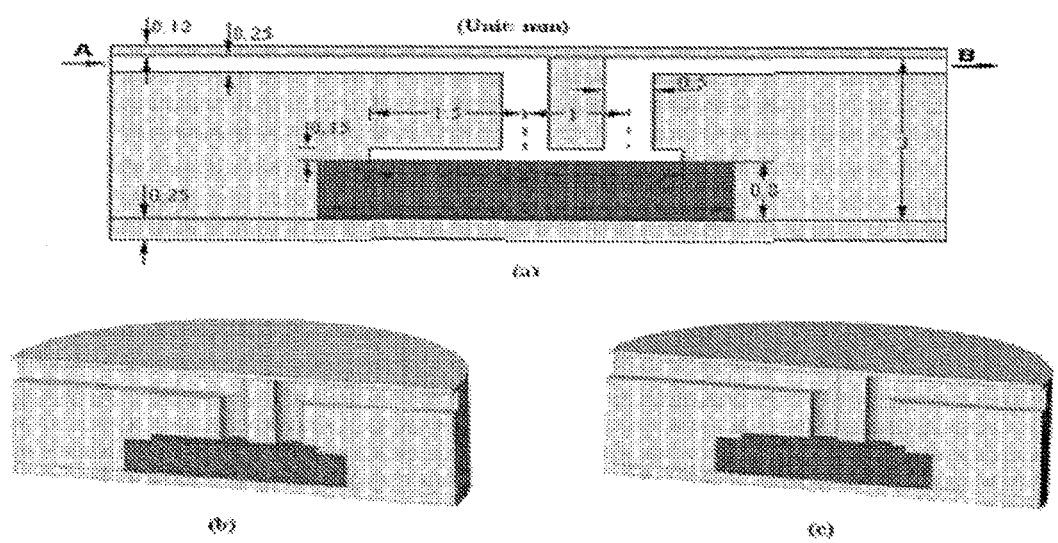
FIG. 17 illustrates an exemplary device that includes a heat-sensitive sealer material.
Figure 18:
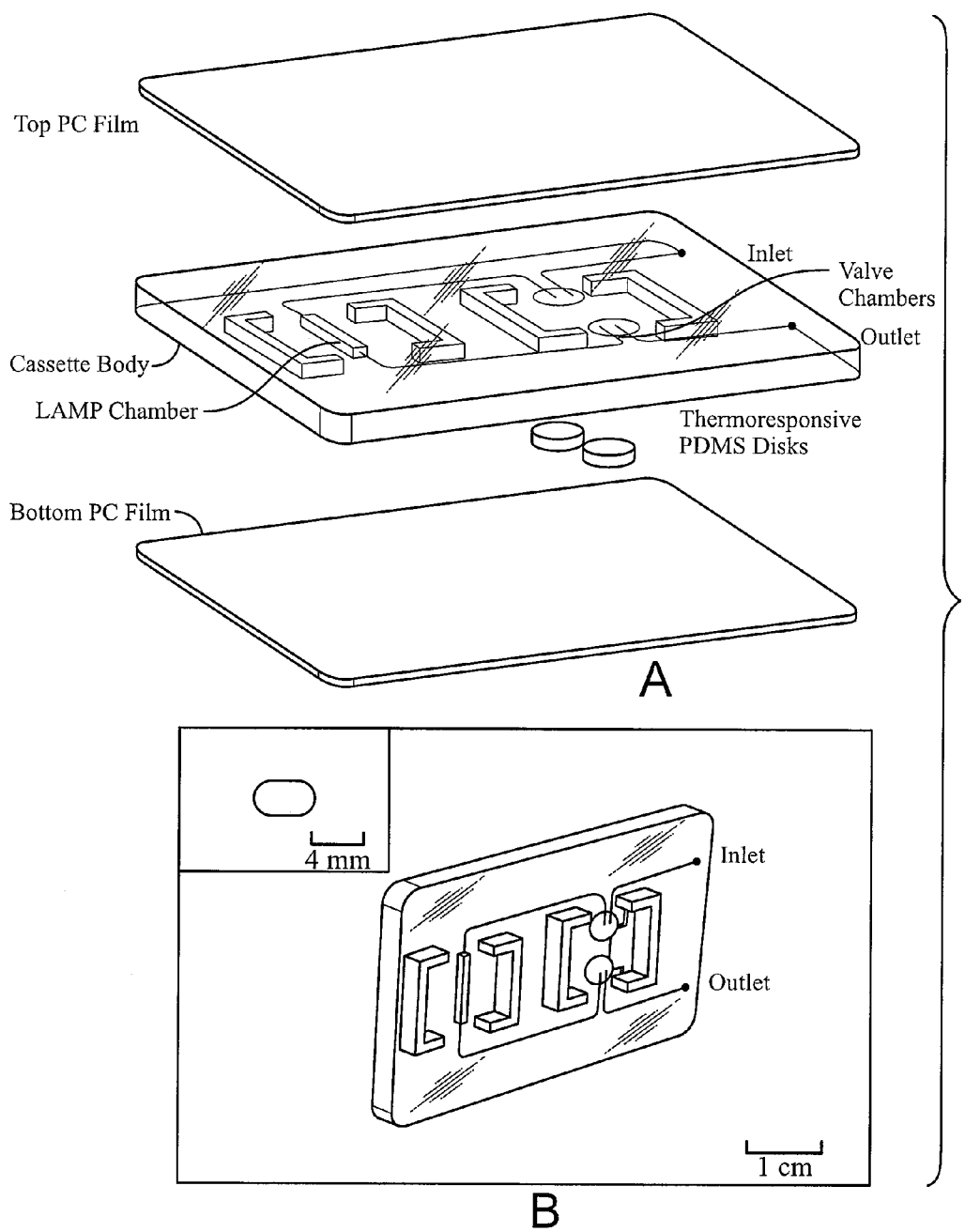
FIG. 18 illustrates an exploded view of a device that includes a heat-sensitive sealer material.
Figure 19:
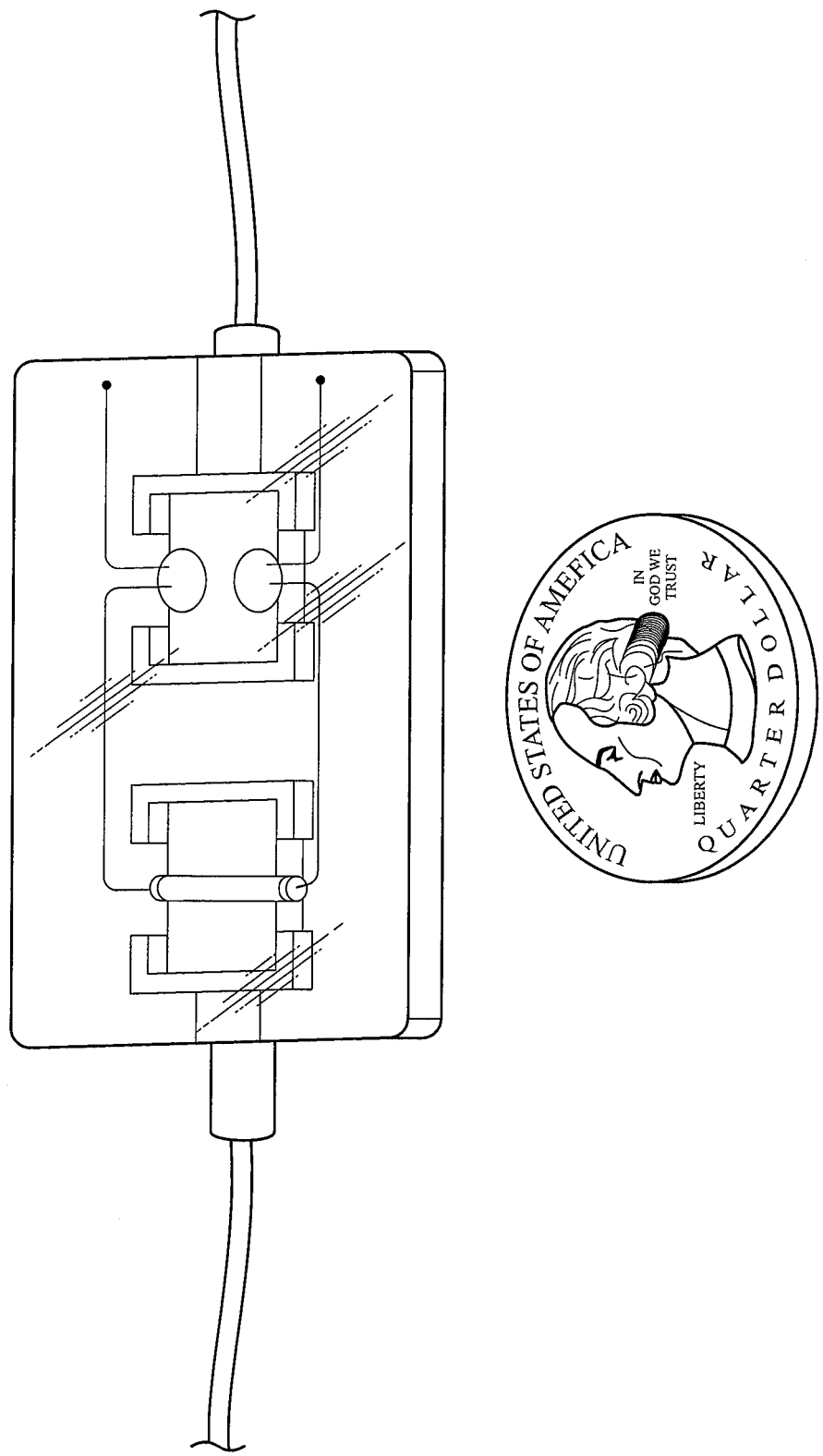
FIG. 19 illustrates a view of a LAMP device that includes electric resistive heaters, which view includes a quarter dollar coin for scale.
Figure 20:
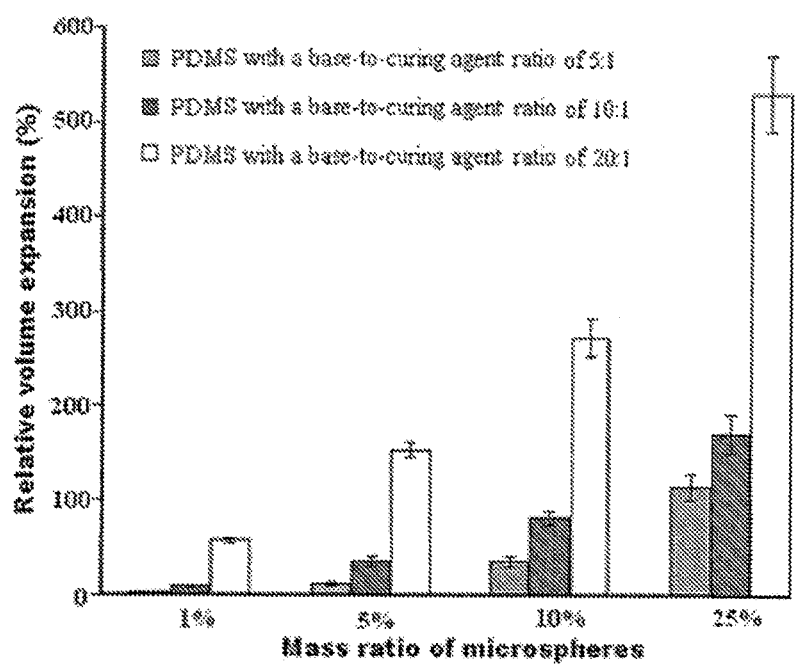
FIG. 20 illustrates the relative expansion for different PDMS (base:curing agent) and mass ratio of Expancel™ microspheres.
Figure 21:
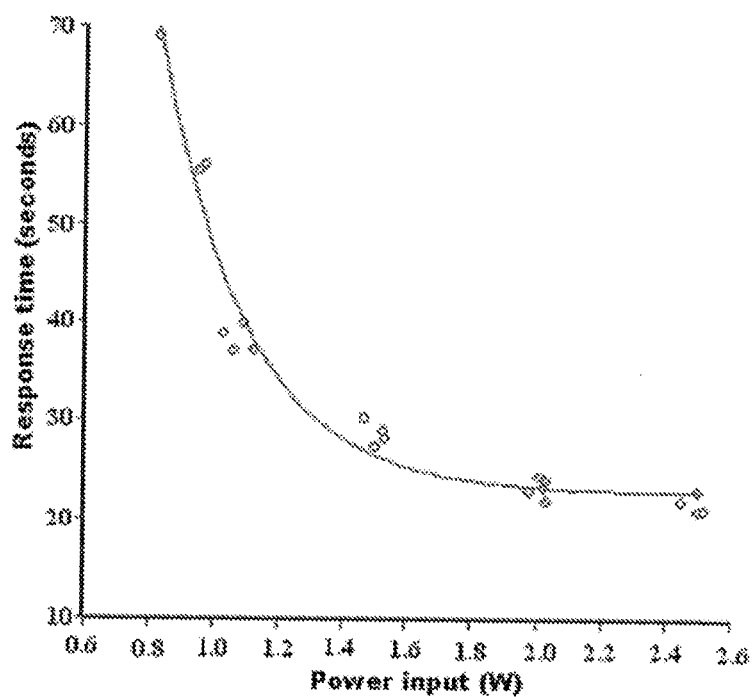
FIG. 21 illustrates the response time of thermally-activated PDMS valves with embedded Expancel microspheres as a function of power input to a heater.

In some embodiments—as shown in FIG. 17 and FIG. 18, described below—the device may include a heat-expanding material disposed so as to obstruct a passage to the chamber when the heat-expanding material is heated. The material may be disposed so as to swell and consequently seal a reaction chamber during nucleic acid amplification. The disclose devices may also include a dry-stored agent, an encapsulated reagent, or both disposed within the device. Such reagents include enzymes, buffer salts, and the like—the on-board storage in turn renders the reagents available when and where needed.

The present disclosure also provides devices that include a chamber; and a capture material that preferentially binds nucleic acids, the capture material being positioned such that the capture material is capable of fluid communication with the interior of the reaction chamber. The capture material may be, as shown in exemplary FIG. 1, so that the capture material resides between an inlet and an outlet of the chamber. The devices may include a nucleic acid amplification agent, a dye, or both—such materials may be dry-stored or encapsulated within the chamber. Alternatively, the materials may be stored in a pouch or other container that is or may be placed into fluid communication with the chamber. The devices may also include a heater that is adapted to heat material disposed within the chamber. The heater may be a thin film heater or other heater; a variety of heaters will be known to those of ordinary skill in the art.

A user may also include a device capable of detecting a dye disposed within the chamber. Such a device may be a camera, a fluorometer, and the like.

Also provided are methods. The methods suitably include isolating a nucleic acid on a capture material that preferentially binds nucleic acids, the capture material being disposed within a chamber; amplifying, in the chamber, at least a portion of the one or more of the nucleic acids by loop-mediated amplification to give rise to an amplification product comprising one or more amplified nucleic acids; transferring, by capillary action, the amplification product to a pervious medium; and detecting the presence of the amplification product on the pervious medium.

In some embodiments, the pervious medium may comprise a lateral flow strip. Such strips may be formed of cellulose, or other fibrous or even particulate matter. A user may label one or more of the amplified nucleic acids (i.e., the amplification product) with a dye, label, or other tag that may facilitate detection. The pervious medium may include one or more antibodies, antigens, or other binding moiety that preferentially bind to one or more of the labeled nucleic acids. The antibody, antigen, or other binding moiety may itself include a label. The antibody antigen, or other binding moiety may be selected so as to preferentially bind to a particular nucleic acid.

A user may lyse a biological sample so as to liberate the one or more nucleic acids. The lysing may be effected by methods known in the art, including heating, reagents, sonication, and the like. Transferring the amplification product may be effected by placing the pervious medium into fluid communication with the chamber. Detection may in turn be effected by visualizing the amplification product on the pervious medium.

A user may also delivery one or more fluids to the chamber according to a preprogrammed schedule so as to effect lysing a biological sample so as to liberate nucleic acids, to effect amplifying the nucleic acids, to effect washing of the capture material, or any combination thereof. The fluid delivery may be effected by an automated device that actuates one or more fluid sources. An exemplary method is shown in FIG. 11, described elsewhere herein.

The present disclosure also provides isolating a nucleic acid on a capture material that preferentially binds nucleic acids, the capture material being disposed within a chamber; amplifying, in the chamber, at least a portion of the one or more of the nucleic acids by loop-mediated amplification to give rise to an amplification product comprising one or more amplified nucleic acids; and detecting the presence of the amplification product within the chamber.

Some embodiments of the disclosed devices provide for a capillary flow mechanism using absorbent media, which simplifies flow control. The chip is completely self-contained, all reagents, buffers, and detection reporters are pre-stored on the chip. The invention exploits effects specific to isothermal amplification at relatively low temperatures (65 deg. C.) compared to PCR, and modes of fluid transport effected with combinations of porous membranes and adsorbent materials, and use of these same materials for lateral flow strip chromatography, lysis and nucleic acid isolation, and dry-storage of reagents.

In one embodiment, the LAMP reaction chamber is integrated with a lateral flow strip for detection. Flow-through of sample, washes, and product is achieved by a means where a cantilevered nitrocellulose (or other absorbent material) flow strip is contacted to the porous FTA™ membrane (which plugs the exit orifice of the reaction chamber and otherwise retains the liquid in the reaction chamber) to initiate flow-through by capillary action. When combined with pouches (as per previous disclosures), a simple fluidic actuation system is feasible, without resorting to the use of pumps. The timer mechanism can be used to flex the lateral flow strip for sustained contact with the FTA™ membrane when amplification is complete. Alternatively, the contact can be finger-actuated by the user at some prescribed time in the process. Similar wicking action with absorbent materials can be used to pull sample, washes, and liquids through the FTA™ membrane and reaction chamber. In this version, there would be one or more absorbent membranes that contact the FTA™ membrane in sequence.

FIG. 10 illustrates an exemplary coupling of a lateral flow strip to the reaction chamber, allowing for simple transfer of amplification product to detection vehicle, and thus reducing the complexity of valves and fluid actuation needed. In this exemplary embodiment, the LAMP reaction chamber is integrated with a lateral flow strip for detection. Flow-through of sample, washes, and product is achieved by a means where a cantilevered nitrocellulose (or other absorbent material) flow strip is contacted to the porous FTA™ membrane (which plugs the exit orifice of the reaction chamber and otherwise retains the liquid in the reaction chamber) to initiate flow-through by capillary action. When combined with pouches (as per previous disclosures), a simple fluidic actuation system is feasible, without resorting to the use of pumps. The timer mechanism can be used to flex the lateral flow strip for sustained contact with the FTA™ membrane when amplification is complete. It should be understood that the Whatman FTA™ membrane described herein is exemplary, as other nucleic-acid trapping materials are useful.

Alternatively, the contact can be finger-actuated by the user at some prescribed time in the process. Similar wicking action with absorbent materials can be used (in a programmed sequence, as shown in FIG. 11) to pull sample, washes, and other liquids through the FTA™ membrane and reaction chamber. In this version, there would be one or more absorbent membranes that contacted the FTA™ membrane in sequence. This approach can be distinguished from other microfluidic devices in that fluid flow is driven by capillary forces rather than hydraulic or pneumatically. The pouch actuation in itself does not generate sufficient thrust to push liquids through the FTA™ membrane. Instead, the device relies on capillary forces to pull the liquid contents of the reaction chamber through the membrane plugs. The membrane otherwise (without contact to an absorption pad) resists liquid flow, and the liquid charge stays in the chamber unless the plug membrane is contacted with an absorbing material. This approach eliminates the need for valves for flow-control and sealing to affect a sequence of fluidic operations. The heating can be provided either from above or from below.

FIG. 11 illustrates another, alternative embodiment of the disclosed devices. As shown in the figure, sample material is added to the reaction chamber. Lysis buffer in pouch 1 is added to the chamber by compressing pouch 1 with Force 1. The lysate mixture is incubated for a prescribed time, with optional stirring by magnetic rods that may be turned by a rotating magnet (not shown).

Next, an absorbent sink pad is contacted with force 4 to the porous FTA™ membrane, which wicks in lysed sample to absorption sink pad, emptying chamber. Nucleic acid is adsorbed on the FTA™ membrane plug. Next, pouch 2 is compressed to add wash buffer to the chamber. Then, the absorbent pad is again contacted to the FTA™ membrane to wick the wash through the membrane. Multiple washes can be effected using additional wash pouches. Next pouch 3 is compressed by force 3, to fill the chamber with de-ionized water. The chamber is then heated, by an external heating element (not shown) or by chemical heating (exothermic reaction). The heating releases pre-stored, encapsulated reagents for isothermal nucleic acid amplification. The amplification step proceeds at elevated temperatures for about 20-60 minutes. After amplification, lateral flow strip is contacted to the porous membrane plug. This is made of a material that has low nucleic acid binding. The strip is loaded with amplification product, which is functionalized with antibody or antigen to capture the labeled amplicon. The LF strip loading pad contains reporter particles to enhance detection of product captured on the strip.

Figure 12:
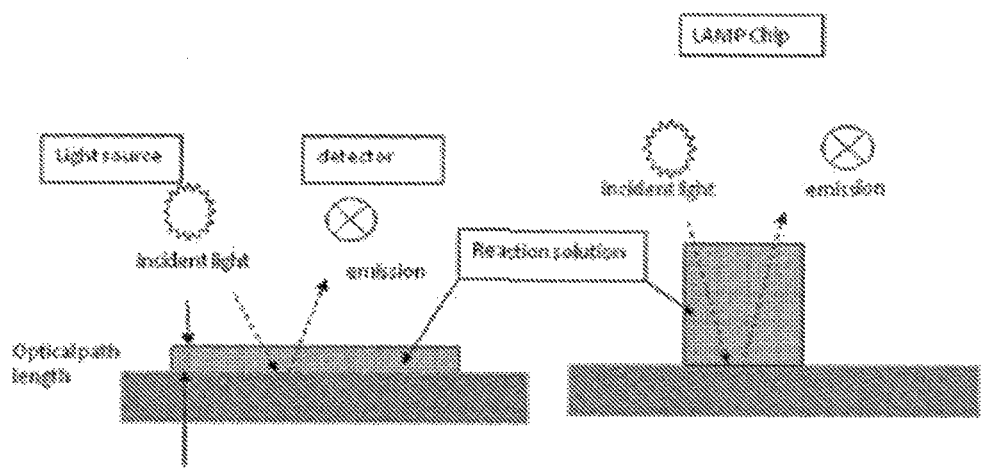
FIG. 12 illustrates a comparison of the depths of various reaction chambers.

Concerning FIG. 12, because of the isothermal nature of the processing, heat transfer in the LAMP chip is not as critical as in PCR chips. In PCR chips, the chamber is made shallow and wide, i.e. with a high lateral width to depth aspect ratio, to facilitate heat transfer with the thermoelectric(s). The geometry of the lamp chip can be changed to better meet other objectives. Accordingly, a LAMP chamber may be relatively deep to increase the optical path length for the fluorescence excitation and generation, which provides a stronger optical signal for real-time detection. For example, a LAMP chamber may have a depth of from 0.01 cm to 10 cm, or from 0.1 cm to 1 cm. The LAMP chamber may have an aspect ratio (height to width) in the range of from 0.1 to about 100, with a range of 1 to 10 being especially suitable.

Exemplary FIG. 13 and FIG. 14 illustrate mechanically-actuated analysis devices. The pouches depression uses a mechanism featuring a timer-actuated microfluidic device. Such a mechanism (with actuating balls that produce forces) may be deployed from the underside of the chip to effect the programmed force actuation of the cantilevered porous strips, so that they contact and de-contact the porous filters that plug the bottom of the reaction in the desired sequence. The rotating disc can also include a permanent magnet to effect stirring via the magnetic stir bars in the reaction chamber.

FIG. 17 presents an embodiment wherein thermally-activated valves with expandable polymer spheres embedded in a PDMS layer (shown by darker shaded areas). These may be incorporated into hard plastic materials such as acrylic and polycarbonate. Expancel™ spheres are hydrocarbon-filled polymer spheres that irreversibly expand when heated to about 70-80 C, and are suitable for the disclosed devices. The inflated spheres expand the PDMS matrix slab, which constricts flow through the channel. This can be used, for example, to seal the reaction chamber during the amplification step. FIG. 18 presents an exemplary use of such thermally-expanding devices. As shown in the figure, thermoresponsive discs (e.g., PDMS) are incorporated into a devices such that the discs are positioned to occlude the inlets or outlets formed in the device upon application of heat. This may be used, for example, to seal the LAMP chamber during amplification.

The following further embodiments are illustrative only and do not limit the scope of the present disclosure.

Materials

HIV virus with a known concentration (confirmed by an independent laboratory) was purchased from ABI Advanced Biotechnologies (MD, USA). Oral fluid samples were formulated by spiking HIV-1 MN strains of various viral loads into whole mouth saliva (WMSS) obtained from healthy, consenting volunteers. For safety reasons, the HIV saliva samples were inactivated with a binding/lysis buffer (Roche Diagnostic, Indiana, USA) in a biosafety facility. The High Purity™ viral RNA Kit, which includes binding/lysis buffer, inhibitor removal buffer, and wash buffer, was provided by Roche Diagnostic (Indiana, USA). The Loopamp RNA amplification kit (RT-LAMP) was obtained from Eiken Chemical Co. Ltd. (Tochigi, Japan). SYTO-9 Green DNA binding dye was obtained from Invitrogen. Acetonitrile, ethanol, and Tris-acetate-EDTA (TAE) buffer (10×) were purchased from Sigma Aldrich and used without further purification. The FTA™ card was obtained from Whatman (Florham Park, N.J.). A mobicol spin mini-column was purchased from MoBiTec (Gottingen, Germany). A 0.118 inch thick poly(methyl methacrylate) (PMMA) sheet and a 0.01 inch thick, PMMA film were, respectively, supplied by McMaster-Carr and Cyro Industries.

Design and Fabrication of the Integrated LAMP Cassette

An exemplary nucleic acid amplification cassette is shown in FIG. 1. FIG. 1A is an exploded view of the cassette. The 46 mm×36 mm×3.50 mm cassette consists of three layers: a top made of 250 mm (0.01 inch) thick, poly(methyl methacrylate) (PMMA) film; a 3 mm (0.118 inch) thick, PMMA cassette body; and a 250 mm (0.01 inch)

thick, PMMA film bottom. Both the top and bottom cover films were cut with a CO2 laser (Universal Laser Systems). The cassette body was milled with a precision, computer-controlled (CNC) milling machine (HAAS Automation Inc.) to form the reaction chamber, membrane support, and access conduits. The various layers were solvent-bonded with acetonitrile at room temperature. Residual solvent was removed by overnight heating at 50° C.

Figure 2:
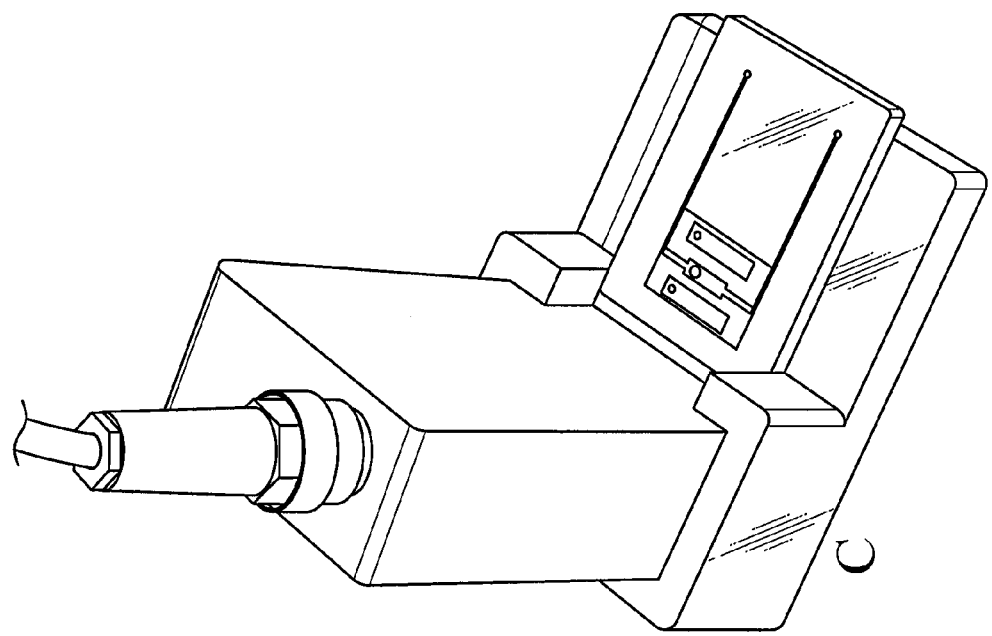
FIGS. 2A, 2B, and 2C depict a microfluidic cassette and an experimental setup for real-time detection of loop mediated isothermal amplification ("LAMP") products.
Figure 2:
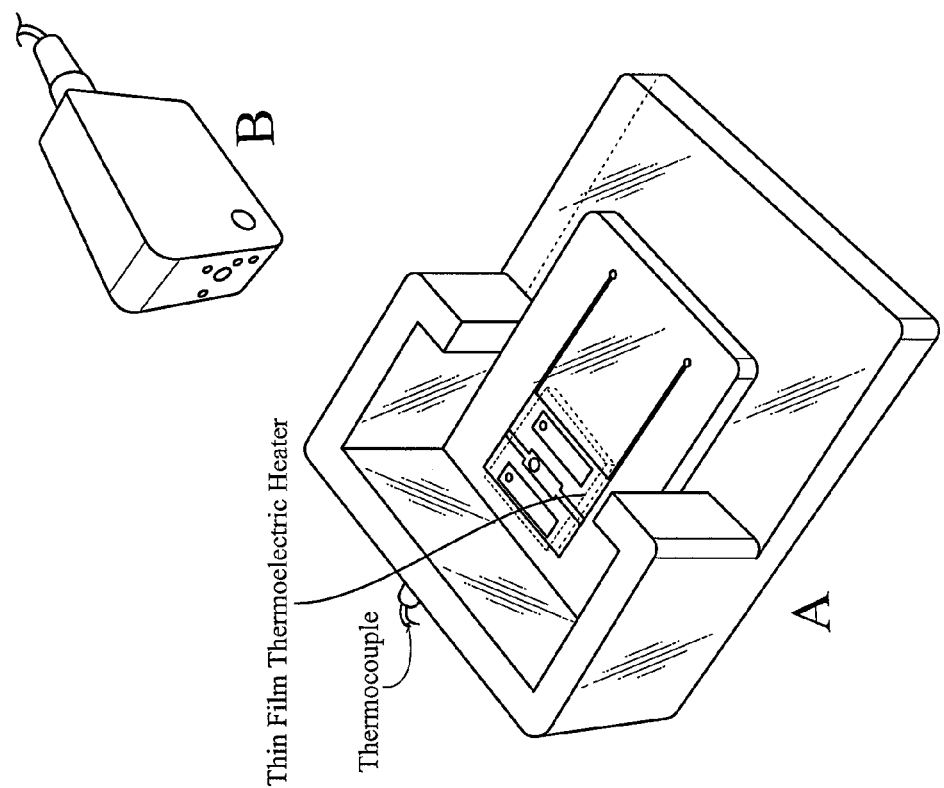

The reaction chamber was connected to the inlet and exit ports with 500 mm wide×200 mm deep conduits. The FTA™ membrane disc was installed at the interface between the inlet port and the reaction chamber. To support the 500 mm thick, FTA™ membrane, two sets of protrusions (ledges) were machined at the bottom and top of the reaction chamber (FIG. 1B and inset). The ledges are shown in detail in the inset of FIG. 1B. The ledges protrude 500 mm from the bore surface and are 300 mm wide and 200 mm tall. The vertical distance between the lower and upper ledges is 500 mm. FIG. 1C depicts schematically an enlarged view of the reaction chamber with the installed FTA™ membrane. A detailed view of the membrane fixed in its supporting ledges is shown in the inset of FIG. 1C. The membrane separates the reaction chamber into a top, main compartment and a bottom compartment. The top compartment is 10.0 mm in length, 2.0 mmin width, and 1.0 mmin height. The bottom compartment is 2.5 mm in length, 1.5 mm in width, and 0.02 mm in height. The total volume of the reaction chamber is ~20 µl. The FTA™ membrane, which is installed between the cassette's inlet and the reaction chamber, acts as a filter for nucleic acid purification, and blocks the introduction of air bubbles into the reaction chamber. FIG. 2A is a photograph of the completed cassette with the integrated FTA™ membrane.

Operation of the Integrated LAMP Cassette

100 µl of the saliva sample (deactivated with lysis buffer) was pipetted into the cassette through the inlet port. The lysed saliva sample filtered through the FTA™ membrane, which wholly intercepted the flow path to bind nucleic acids contained in the saliva sample. In other words, the membrane isolated and concentrated the RNA molecules from the saliva sample. Next, 100 µl of Roche inhibitor removal buffer was pipetted into the cassette to remove any amplification inhibitors that may have been present in the saliva. Then, the FTA™ membrane was washed twice with 200 µl of wash buffer, followed by air-drying for 30 seconds. Next, 22 µl of LAMP master mixture, which contained all the reagents necessary for the RT-LAMP and fluorescent dye (SYTO® 9 Green), was injected into the reaction chamber through the inlet port. Subsequently, the inlet and outlet ports were sealed using transparent tape (Scotch tape, 3 M, St Paul, Minn.) to minimize evaporation during the amplification process.

Real-Time RT-LAMP for HIV Detection

The LAMP primers were designed by Curtis et al. at the Center for Disease Control and Prevention (CDC) and provided to New York University through a Material Transfer Agreement. The six RT-LAMP primers[15,16] have been designed against the highly conserved sequences located within the p24 gene region. The primers and their respective concentrations were: outer primer F3 50-ATTATCA-GAAGGAGCCACC-3' (0.2 µM), outer primer B3 50-ATC-CTATTTGTTCCTGAAGG-3' (0.2 µM), loop primer F loop 50-TTTAACATTTGCATGGCTGCTTGAT-3' (0.8 µM), loop primer B loop 50-GAGATCCAAGGGGAAGTGA-3' (0.8 µM), inner primer BIP 50-TGTTGCACCAGGCCA-GATAATTTTGTACTGGTAGTTCCTGCTATG-3' (1.6 µM) and inner primer FIP 5'-CAGCTTCCTCATTGATG-GTTTCTTTTTAACACCATGCTAAACACAGT-3' (1.6 µM).

The LAMP master reaction mix also contained 20 mM Tris-HCl (pH 8.8), 10 mM KCl, 10 mM (NH2)SO4, 8 mM MgSO4, 0.1% Tween 20, 0.8 M betaine, 8U Bst DNA polymerase (New England Biolabs, Inc., MA), 0.625U AMV reverse transcriptase (Invitrogen, Carlsbad, Calif.), 1.4 mM dNTPs, and 4.0 µM SYTO® 9 Green (Molecular Probes, Inc., Eugene, Oreg.).

In addition to real-time fluorescence detection, LAMP reaction products were subjected to gel electrophoresis. 5 µl of each LAMP-amplified product was loaded onto a lane of a 2.0% agarose gel. Electrophoresis of the amplified DNA fragment was carried out in 1×TAE buffer (Tris-acetate-EDTA) at a constant voltage of 115 V. DNA molecular mass markers (Roche Diagnostic, Indianapolis, Ind., USA) were used to estimate the sizes of the various amplified products. The gel was stained with ethidium bromide and visualized with UV illumination.

Portable, Real-Time LAMP Apparatus

An exemplary setup for the integrated LAMP cassette is shown in FIGS. 2A and 2C. The system consisted of a cassette holder equipped with a flexible, polyimide-based, thin film heater (Model HK5572R7.5L23A, Minco Products, Inc., Minneapolis, Minn.), a thermocouple located at the interface between the heater and the cassette, and a portable, compact optical detector. The fluorescence excitation and detection were carried out with a minute, portable ESE optical detection system (Fluo Sens SD 003, ESE GmbH, Stockach, Germany).

The ESE optical detector consists of a 470 nm, light-emitting diode as the excitation light source and a low-noise, Si-photodiode for fluorescence detection. The detector was interfaced with a computer through a USB interface. A software program was written to display a graph of the fluorescence intensity as a function of time. FIG. 2B shows the cassette holder with the cassette and FIG. 2C shows the cassette holder with the reader in place and the cassette prior to its insertion into the cassette holder.

When the integrated LAMP cassette, filled with LAMP master mixture, was inserted into the cassette holder, the reaction chamber formed a thermal contact with the thin film heater positioned in the cassette holder. The heater was powered with a DC power supply (Model 1611, B&K Precision Corporation, CA) and the reaction chamber's temperature was controlled in an open-loop mode. Calibration was accomplished by building a mock cassette, filling the reaction chamber with water, and inserting a type-K thermocouple (Omega Engr., each wire 75 µm in diameter, and a junction diameter of ~170 µm) into the chamber. The thermocouple reading was monitored with a HH506RA multilogger thermometer (Omega Engr., Stamford, Conn., USA) and correlated with the power input.

To further determine the reaction's specificity, the amplicon's melting curve was determined A custom software program directed the power supply to gradually increase the amplification chamber's temperature from 55° C. to 90° C. Both the chamber's temperature and the fluorescent signal intensity were continuously recorded and the fluorescent intensity was displayed as a function of the reaction chamber's temperature.

Benchtop LAMP Experiments

Prior to testing the isothermal amplification in the cassettes, benchtop studies were performed. In the first set of experiments (without filtration and purification), saliva samples were directly mixed with the RT-LAMP master mixture in a PCR vial, and then incubated at 60° C. for 60 min followed by 5 min at 80° C. to inactivate the polymerase activity in the thermal cycler (PTC-220 DNA Engine Dyad_Peltier Thermal Cycler).

In the second set of experiments, an FTA™ membrane was tested for isolating RNA from saliva and removing substances that inhibit enzymatic amplification. An FTA™ membrane was fitted to a Mobicol spin mini-column. 100 ml of spiked saliva samples were spun through the membrane at 14 000 rpm for 30 s, followed by 100 µl of inhibitor removal buffer, and additional centrifugation (10 000 rpm, 30 s). The membrane was then washed twice with 200 ml wash-buffer. Each wash was followed by centrifugation (10 000 rpm, 30 s). The column was then spun for one minute to dry the membrane at 14 000 rpm. Next, the FTA™ membrane was removed from the spin mini-column and inserted in a PCR vial together with the RT-LAMP reagents, and incubated at 60° C. for 60 min followed by 5 min at 80° C. Subsequent to the amplification process, each amplification product was subjected to gel electrophoresis in a 2% agarose gel.

Results

Inhibition Effect of Saliva on RT-LAMP

Figure 3:
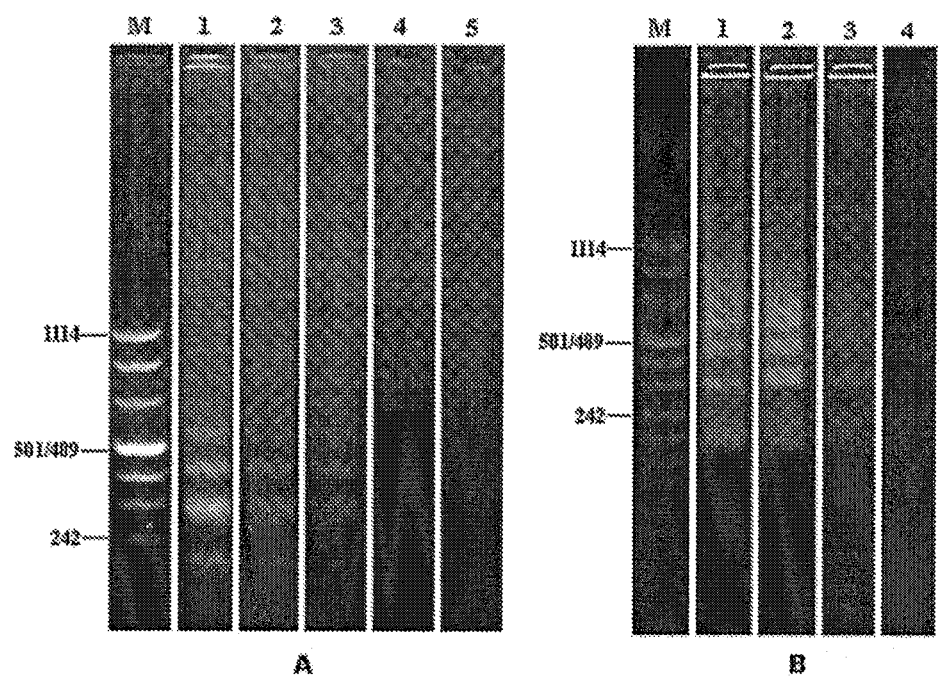
FIG. 3 presents electropherograms of HIV RT-LAMP amplicons obtained according to the present disclosure with saliva samples spiked with HIV without purification (A) and with FTA™ membrane-based purification (B). (A) Lane M: DNA marker; lane 1: 107 HIV particles per ml; lane 2: 106 HIV particles per ml; lane 3: 105 HIV virus particles per ml; lane 4: 104 HIV particles per ml; and lane 5: negative control. (B) Lane M: DNA markers; lane 1: 104 HIV particles per ml; lane 2: 103 HIV particles per ml; lane 3: 102 HIV particles per ml; and lane 4: negative control. The electrophoresis separation processes (A) and (B) were carried out for different lengths of time.

Prior studies revealed the presence of PCR inhibitors in saliva. To explore the impact of salivary inhibitors on the LAMP process, a benchtop dilution study ($10^7$ to $10^4$ virions per ml) was performed. The resulting electropherograms are shown in FIG. 3A. Lane M is the DNA ladder (Roche DNA Molecular Weight Marker VIII). Lanes 1, 2, 3, 4, and 5 correspond, respectively, to $10^7$, $10^6$, $10^5$, $10^4$, and 0 (negative control) HIV virus particles per ml. Due to the sample size, the actual number of virus particles in the vial was ten-fold smaller.

The experiment was repeated in triplicate with similar results. LAMP amplification products consist of stem-loop DNA structures with inverted repeats of the target and cauliflower-like structures with multiple loops. Consequently, the LAMP amplicons have different lengths and the corresponding electropherograms feature a characteristic, ladder-like pattern, which consists of many bands of different lengths all the way up to the loading well. Lanes 1, 2, and 3 exhibit the characteristic pattern of LAMP electropherograms. The bands of the shorter segments are located approximately at positions corresponding to $n \times 115$ bp, where n=2, 3, and so on.

A solid state membrane (FTA™) fitted into a spin column format was used to explore removal of inhibitors from saliva prior to amplification. The electropherogram of the resulting LAMP amplicons is shown in FIG. 3B. Lane M is the DNA ladder. Lanes 1, 2, 3, and 4 correspond, respectively, to $10^4$, $10^3$, $10^2$, and 0 (negative control) HIV particles per ml.

The experiment was repeated in triplicate with similar results. When a FTA™ membrane was used as a solid phase extraction (SPE) matrix to purify viral RNA from oral fluid, one could detect down to $10^2$ virions per ml, which corresponds to 10 virus particles in the sample. In other words, with the FTA™ membrane based purification, one could improve the detection limit a thousand fold. Without being bound to any single theory, this demonstrates that the FTA™ membrane effectively purified nucleic acids, allowed the removal of potential inhibitors from the saliva sample, and dramatically improved the detection sensitivity of the RT-LAMP process. Moreover, the experiment demonstrates the compatibility of FTA™ with the LAMP amplification process. In other words, the presence of the FTA™ membrane in the reaction vial does not adversely impact the efficiency of the LAMP process.

Integrated LAMP Cassette

A LAMP cassette body was abricated using CNC machining technology, which can mill a variety of complex three-dimensional (3-D) microstructures. In mass production, it is anticipated that the cassette would be fabricated by injection molding. To enhance the nucleic acid extraction efficiency, a flow-through mode was adopted in one design. The saliva sample, mixed with binding/lysis buffer, flows through the membrane, and nucleic acids from the sample bind to the membrane (FIG. 1C). Once wet, the FTA™ membrane expands and seals against the chamber walls, preventing the sample from bypassing the membrane.

Because amplification occurs at a constant temperature, the integrated LAMP cassette does not require precise thermal control as in conventional PCR. A single, thin film heater and open loop control were sufficient for performing the LAMP reaction. The heater may also be patterned on the cassette directly.

Real-Time, RT-LAMP for HIV Detection

Figure 4:
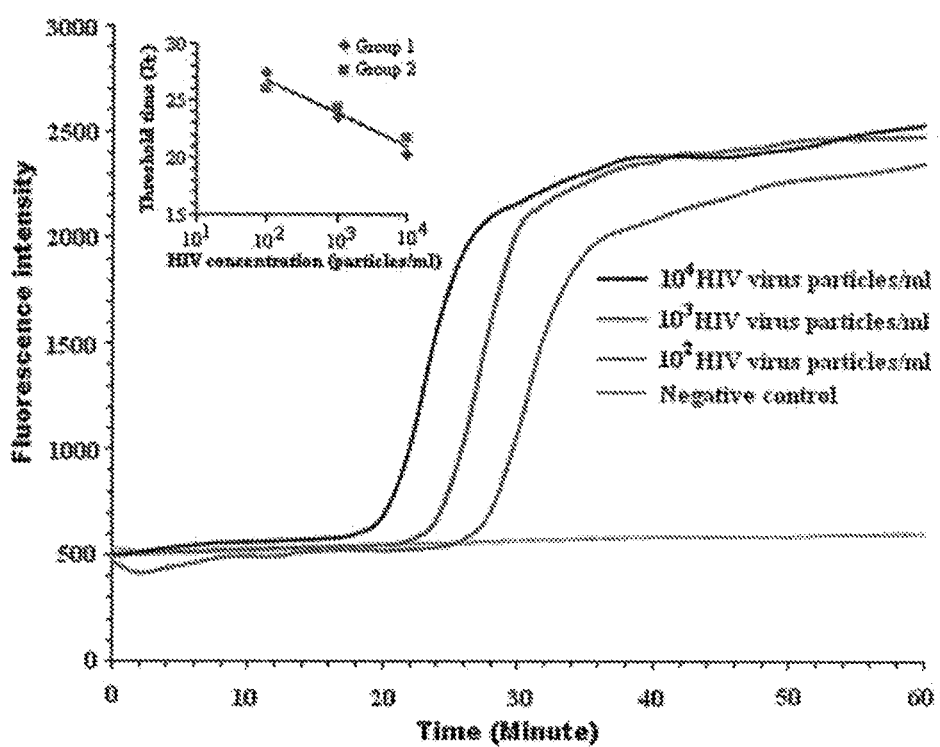
FIG. 4 presents real-time monitoring data for RT-LAMP amplification of saliva samples containing $10^4$, $10^3$, $10^2$, and 0 (negative control) HIV particles per ml. Inset: the threshold time $T_t$ (min) as a function of the HIV concentration (particles per ml).

FIG. 4 depicts real-time fluorescence intensity as a function of time detected from a cassette when the saliva test sample contained $10^4$, $10^3$, $10^2$, and 0 (negative control) HIV particles per ml corresponding to 103, 102, 10, and 0 (negative control) HIV particles in the sample. The fluorescent intensity of the negative control (no target) remains nearly level throughout the entire detection time, indicating negligible amplicon formation, if any, of primer-dimers and the absence of any significant contamination. When HIV was present, the signal intensity increased from a baseline of about 500 relative fluorescent units (RFU) to the saturation level of the detection system. The higher the target concentration was, the earlier the intensity curve increased above the baseline. The LAMP amplicons from the lowest sample concentration (10 HIV particles in the reactor) registered a visible increase in emitted fluorescence intensity at approximately 27 min. Beyond this time, the signal intensity increased rapidly, reaching a saturation level at about 36 min. Thus, in a point of care setting, the test could terminate in less than 40 min, although this figure is exemplary only and is not necessarily a limit to the speed of the test. The results indicate that as few as 10 HIV particles can be detected with relatively unsophisticated equipment. The tests were repeated twice with nearly identical results.

The threshold time ($T_t$) is defined as the reaction time that elapses until the florescent signal increases ~20% above the baseline level. FIG. 4 indicates that $T_t$ increases as the target molecule's concentration C (HIV virons per ml) decreases. FIG. 4 (inset) depicts the threshold time $T_t$ (min) as a function of C on a semi-log plot. In the range $10 < C < 1000$ viral particles per reaction chamber, the threshold time $T_t$ decreases linearly as a function of log (C). The data can be correlated with the formula $T_t \approx 32.6 - 2.9 \log(C)$, where $T_t$ is expressed in min.

The amplification results were monitored in real time with a compact, portable fluorescent detector, which simplifies cassette design and eliminates the need to transfer the reaction products from the amplification chamber to a detection chamber. Real-time detection also reduces the analysis time since the test can be terminated as soon as the threshold time ($T_t$) is determined.

Specificity of RT-LAMP

Figure 5:
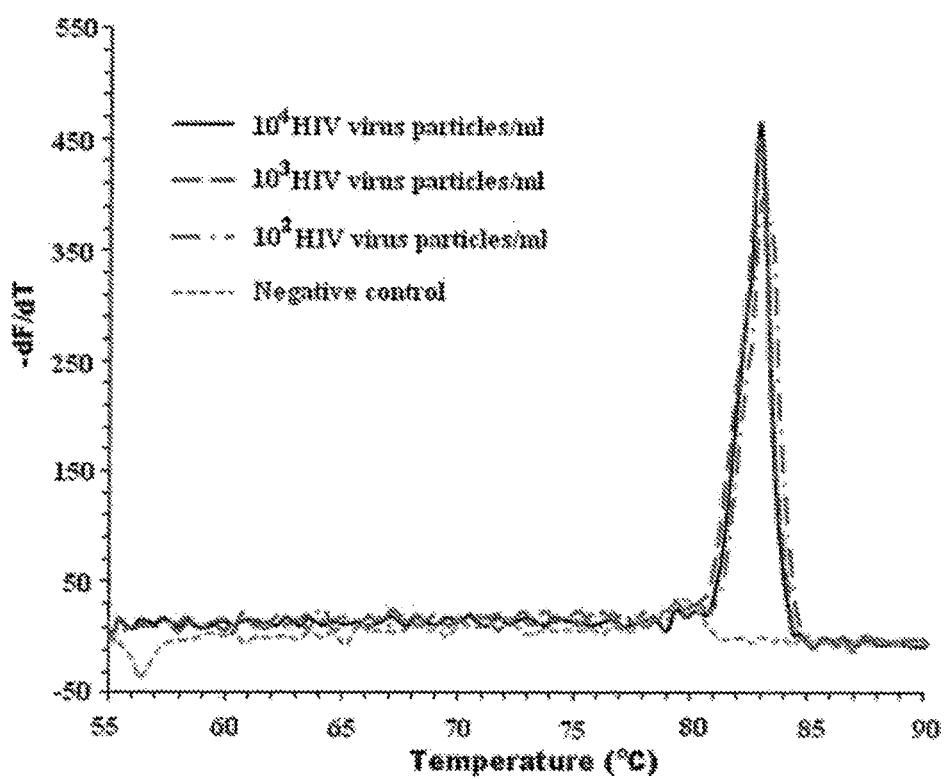
FIG. 5 illustrates the derivative of the fluorescence intensity with respect to the temperature, dF/dT, is depicted as a function of the temperature when the analyte consisted of $10^4$, $10^3$, $10^2$ and 0 (negative control) HIV particles per ml.

To determine the reaction specificity, the melting curve shown in FIG. 5 was obtained. At the conclusion of the RT-LAMP amplification process, the reaction chamber's temperature was increased gradually from 55° C. to 90° C. while monitoring the fluorescence emission. When the temperature reached the melting temperature of the amplicons, the fluorescent signal intensity diminished greatly. Although the LAMP amplicons have different lengths, as is evident from the electropherograms (FIG. 3), in the absence of non-specific binding, the double stranded segments of each amplicon have the same length and thus a single melting temperature (as observed). Using finite differences, one may calculate the derivative of the emission intensity with respect to the temperature dF/dT, where F is the emission intensity expressed in RFU and T is the reactor temperature expressed in ° C. FIG. 5 depicts dF/dT as a function of T when there are $10^4$, $10^3$, $10^2$ and 0 (negative control) HIV particles per ml. In the absence of target analytes (negative control), dF/dT remains level for the entire temperature range. When target analyte and amplification products are present, the curves feature sharp peaks centered at a melting temperature ($T_m$) ~83° C. Using the Nearest-Neighbor module of Oligo Calc: Oligonucleotide Properties Calculator (http://www.basic.northwestern.edu/biotools/oligocalc.html), one may estimate the melting temperature of the amplicon to be 83.5° C., which is in good agreement with the measured value of 83° C. (FIG. 5).

To assess whether the melting temperature measurement could reveal the presence of primer-dimers that could potentially lead to a false positive result, one may estimate the melting temperatures of various hypothetical primer-dimers that could form in a LAMP process. For these estimates, it was assumed that the hypothetical primer-dimers are formed by end-to-end joining of forward and reverse primers. As there are a total of three forward and three reverse primers used in LAMP, there are nine distinct potential primer-dimer combinations. Listed below are the possible primer-dimers and their estimated melting temperatures ($T_m$) as calculated using the Nearest-Neighbor module of the Oligo Calc. These are FIP-BIP (92 bp, estimated Tm ¼ 77.5° C.), FIP-LoopB (66 bp, $T_m$=74.0° C.), FIP-B3 (68 bp, est. $T_m$=72° C.), LoopF-BIP (70 bp, est. $T_m$=74° C.), LoopF-LoopB (44 bp, est. $T_m$=68° C.), LoopF-B3 (46 bp, est. $T_m$=68° C.), F3-BIP (64 bp, est. $T_m$=75° C.), F3-LoopB (38 bp, est. $T_m$=68° C.), and F3-B3 (40 bp, est. $T_m$=67.5° C.). The melting temperatures of the various hypothetical primer-dimers are more than 5° C. below the melting point of the target amplicon. Thus, the melting temperature curve is capable of distinguishing between target amplicon and primer-dimers. No primer-dimer formation was detected.

Figure 6:
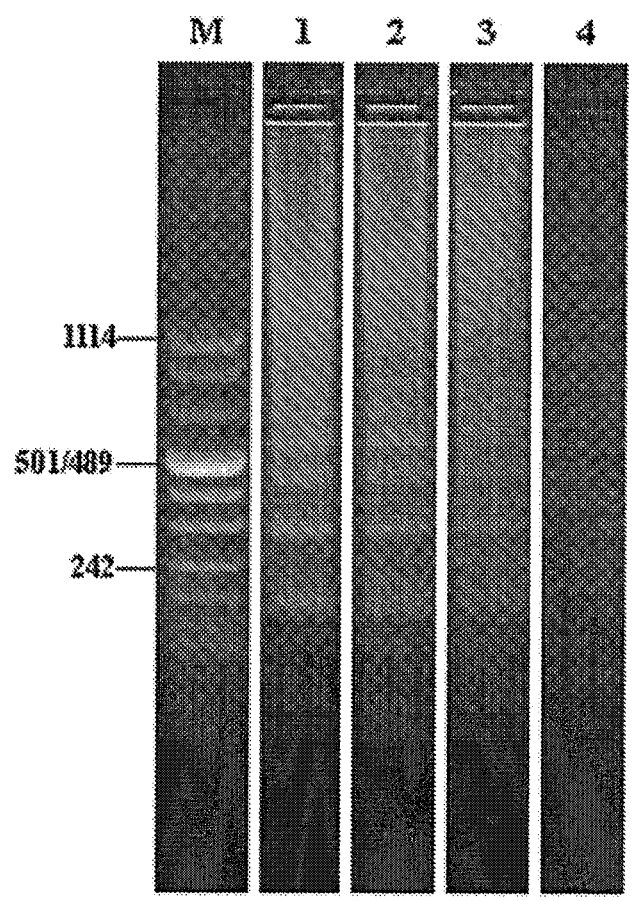
FIG. 6 illustrates electropherograms of RT-LAMP products obtained with integrated LAMP cassette. Lane M is DNA ladder markers and lanes 1, 2, 3, and 4 correspond, respectively, to $10^3$, $10^2$, 10, and 0 (negative control) HIV particles per reaction chamber.

The results of the real-time LAMP measurements were further confirmed by agarose gel electrophoresis (FIG. 6). Lane M is DNA ladder markers. Lanes 1, 2, 3, and 4 correspond, respectively to $10^3$, $10^2$, 10 and 0 (negative control) viral particles in the reaction chamber. The negative control exhibited no signal. The electropherograms of the three positive samples showed band patterns characteristic of LAMP amplicons and consistent with the benchtop results (FIG. 3B). Thus, FIG. 6 indicates that the integrated LAMP cassette produced amplification results comparable with the benchtop experiments. The lack of bands corresponding to amplicons shorter than 220 kb indicates that no significant amounts of primer-dimer were formed, which is consistent with the observed melting curve (FIG. 5).

Figure 7:
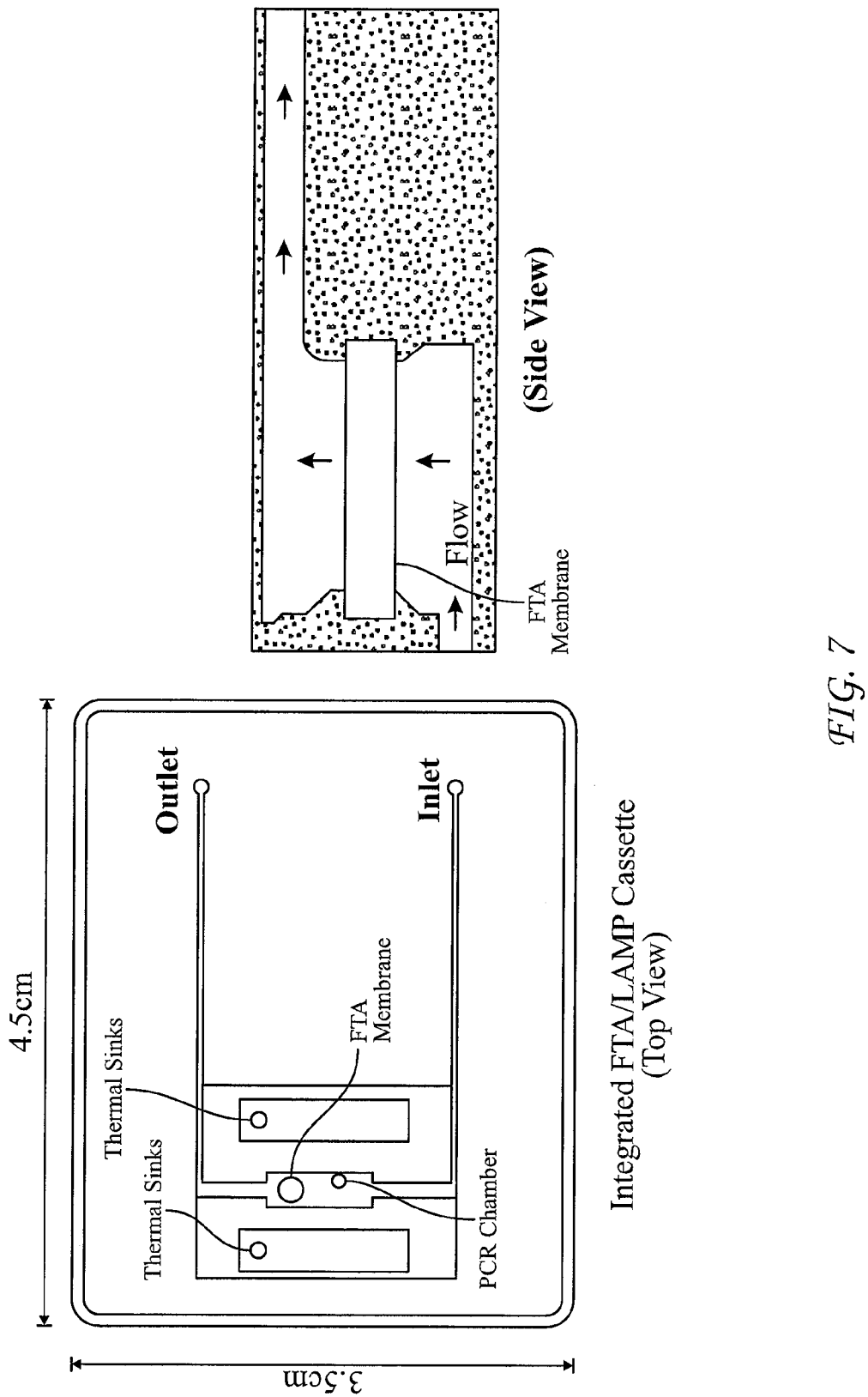
FIG. 7 illustrates a module (top view) containing a nucleic acid amplification reactor (left). A cross-section (right) shows sample flows through an isolation membrane.

An alternative view of the an integrated, multifunction, isothermal amplification chamber is shown in FIG. 7. The amplification chamber (e.g., 10-20 µl volume) enables nucleic acid isolation, concentration, purification, amplification, and detection. The amplification chamber may, as described, store encapsulated (thermally-released) dried reagents needed for DNA amplification. In the event of low abundance analytes, sample volume can exceed the amplification chamber volume. Pre-stored reagents (not shown in FIG. 7) are released and hydrated when needed when the chamber's temperature exceeds the release temperature of the encapsulant. This temperature can be in the range of from 35 deg. C. to 60, 70, or even 80 deg. C., depending on the encapsulant.

Figure 8:
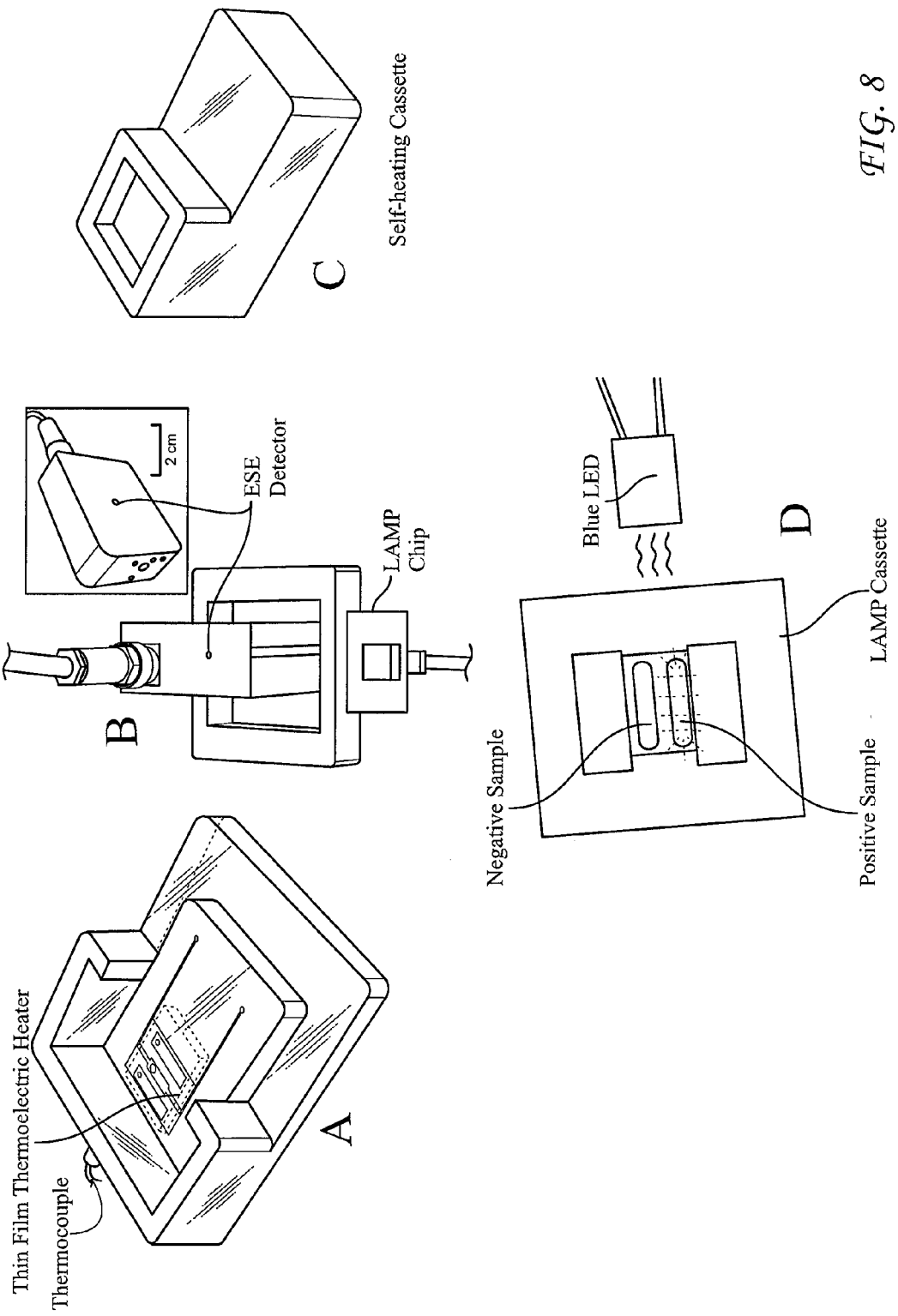
FIGS. 8A, 8B, 8C, and 8D illustrate an experimental set-up used in connection with the disclosed devices.
Figure 9:
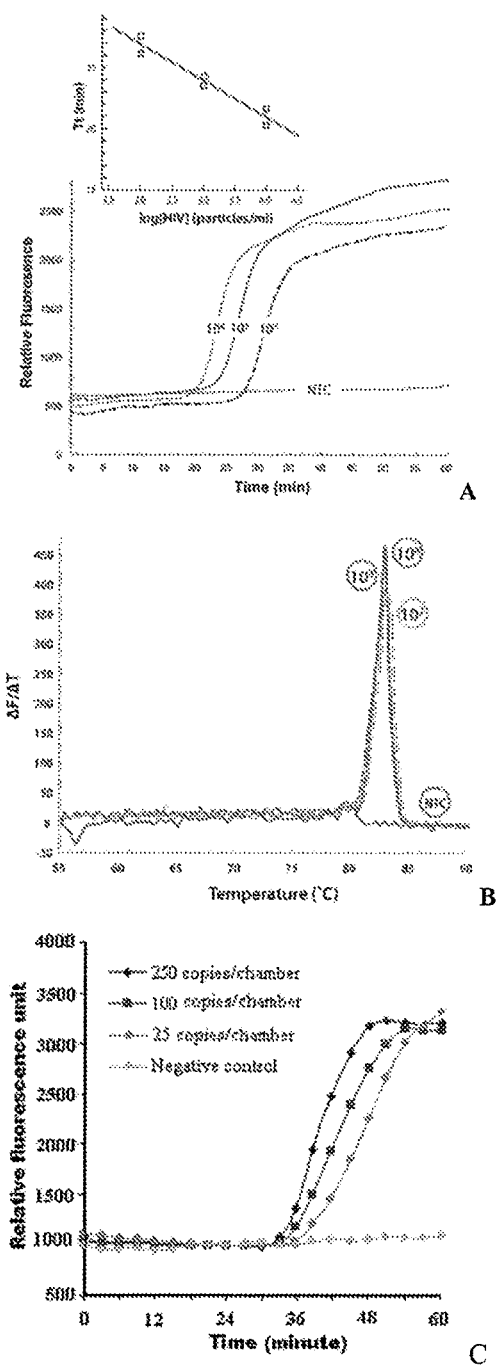
FIG. 9 presents (A) Real-time monitoring of Reverse Transcription LAMP of saliva samples laden with $10^4$, $10^3$, $10^2$, and 0 (negative control) HIV particles/ml. The inset shows the threshold time $T_t$ as a function of the HIV concentration (particles/ml). The threshold time is used to quantify the target concentration. (B) A melting curve, showing the derivative of the fluorescence intensity with respect to the temperature is depicted as a function of the temperature when the analyte consisted of $10^3$, $10^2$, 10 and 0 (negative control) HIV particles in the reaction chamber. The peak occurs at a melting temperature consistent with the length of the target amplicon. (C) Real time detection of *Escherichia coli* DNA in the LAMP cassette. The experiments were carried out with cassettes similar to the ones in FIG. 7 and the set-up shown in FIGS. 8 A and B. Similar performance was obtained with the self-heating device.

Arrays of amplification reactors can be accommodated on a single substrate to facilitate multi-analyte detection, control, and calibration. To demonstrate the capabilities of the amplification reactor depicted in FIG. 7, one spiked HIV-1 virus in saliva samples taken from willing (healthy) volunteers and *E.-Coli* in urine. The experimental set-up is shown in FIG. 8. The devices can operate with a simple processor that allows one to obtain quantitative data (FIGS. 8A and B) or as completely un-instrumented, qualitative devices (FIGS. 8C and D). The device shown in FIG. 8C is self-heated. The heating is provided with an exothermic reaction, and the temperature is regulated with a phase change material. Exemplary phase change materials are described in U.S. application 61/488,823, filed on May 23, 2011, the entirety of which is incorporated herein by reference. Amplicons are detected in real time with an intercalating dye (FIGS. 9A and C). Alternatively, the amplification products can be discharged onto a lateral flow strip for detection. The experiments consistently demonstrated a limit of detection better than 100 target molecules/ml sample.

Summary

An integrated, single-chamber LAMP cassette that utilizes a capture material (e.g., FTA™ membrane) for nucleic acid isolation, purification, and concentration is presented. The nucleic acids captured on an FTA™ membrane were directly used as templates for nucleic acid amplification without any need for a special elution and transfer of nucleic acids, which, in turn, greatly simplified chip design and flow control. To demonstrate the system's utility for point of care detection of virus, a series of experiments were done in which one detected HIV particles suspended in raw saliva. The experiments indicated that the single-chamber LAMP cassette system could detect HIV-1 in oral fluid with the sensitivity of 10 HIV particles per reaction chamber within less than an hour, while PCR assays required well over an hour to complete the amplification process. This demonstrates a LAMP reactor with an integrated flow-through membrane.

The cassette may, in some embodiments, include dry storage of the LAMP/RT-LAMP reagents in the reaction chamber. This can be achieved by encapsulating the dry reagents with low melting point paraffin, which melts upon heating the reaction chamber to the desired incubation temperature (e.g., 60° C.) and releases the LAMP reagents for amplification. One may also store buffers for the isolation and purification of nucleic acid in the cassette in a pouch format. Such systems can be used to detect diseases, monitor the health of individuals, provide a trigger for the administration of expensive or dangerous medications, handle samples of body fluids other than saliva, and also facilitate the monitoring of water and food quality. While nucleic acid amplification and detection are used herein to illustrate the disclosed devices, it should be understood that the devices are suitable for detecting other biomolecules, including proteins.

What is claimed:

1. An analysis device, comprising:
a chamber having a first and a second outlet;
a capture material that preferentially binds nucleic acids, the capture material being positioned such that the capture material is capable of fluid communication with the interior of the chamber;
a first pervious body adapted such that the first pervious body and the chamber are capable of relative motion such that the first pervious body is placed into fluid communication with the chamber;
a pervious transport material disposed at an outlet of the chamber; and
a second pervious body, the second pervious body being positionable such that the second pervious body contacts the transport material.

2. The analysis device of claim 1, wherein the first pervious body adapted to be movably positionable such that the first pervious body contacts the capture material.

3. The analysis device of claim 1, wherein the first and second pervious bodies are in register with the first and second outlets, respectively.

4. The analysis device of claim 1, wherein the second pervious body comprises a binding moiety adapted to bind to a nucleic acid communicated from the transport material to the second pervious body.

5. The analysis device of claim 4, wherein the binding moiety comprise an antibody, an antigen, a receptor, a ligand, a nucleic acid, or any combination thereof.

6. The analysis device of claim 1, wherein the second pervious body comprises a reporter molecule adapted to associate with a nucleic acid communicated from the transport material to the second pervious body.

7. The analysis device of claim 1, wherein the second pervious body comprises a lateral flow strip.

8. The analysis device of claim 1, further comprising one or more quantities of fluid stored such that the fluid may be introduced to the interior of the chamber.

9. The analysis device of claim 1, further comprising a device adapted to heat the chamber.

10. The analysis device of claim 1, further comprising a detector capable of detecting the presence of one or more nucleic acids disposed on the second pervious body.

11. The analysis device of claim 10, wherein the detector is exterior to the chamber.

12. The analysis device of claim 10, wherein the detector comprises a camera, a fluorometer, or any combination thereof.

13. The analysis device of claim 1, further comprising a quantity of fluid disposed in a container.

14. The analysis device of claim 13, wherein the container is adapted to deliver the fluid into the chamber.

15. The analysis device of claim 13, wherein the fluid comprises a lysis buffer, a wash buffer, water, a nucleic acid amplification agent, or any combination thereof.

16. The analysis device of claim 13, further comprising a device configured to modulate delivery of fluid into the chamber.

17. The analysis device of claim 16, wherein the device comprises one or more projections adapted to actuate the container so as to deliver fluid to the chamber.

18. The analysis device of claim 16, wherein the device rotates, translates, or both, so as to actuate the container according to a preprogrammed schedule.

19. The analysis device of claim 1, further comprising a heat-expanding material disposed so as to obstruct a passage to the chamber when the heat-expanding material is heated.

20. The device of claim 1, further comprising a dry-stored agent, an encapsulated reagent, or both disposed within the device.

21. The device of claim 1, wherein the second pervious body is in fluid communication with the chamber.

22. The device of claim 1, wherein contact between the first pervious body and the capture material gives rise to a pathway capable of wicking fluid out of the chamber.

23. The device of claim 1, wherein contact between the second pervious body and the transport material gives rise to a pathway capable of wicking amplified nucleic acid out of the chamber.

* * * * *

UNITED STATES PATENT AND TRADEMARK OFFICE
CERTIFICATE OF CORRECTION

PATENT NO.         : 9,476,102 B2
APPLICATION NO.    : 14/001347
DATED              : October 25, 2016
INVENTOR(S)        : Haim H. Bau et al.

It is certified that error appears in the above-identified patent and that said Letters Patent is hereby corrected as shown below:

On the Title Page
Item (75) Inventors:
Delete "Daneil Malamud," and insert -- Daniel Malamud, --.
Delete "Xianbo Ceiu," and insert -- Xianbo Qiu, --.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attatcagaa ggagccacc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcctatttg ttcctgaagg                                                   20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttaacattt gcatggctgc ttgat                                             25

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagatccaag gggaagtga                                                    19

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgttgcacca ggccagataa ttttgtactg gtagttcctg ctatg                       45

<210> SEQ ID NO 6
<211> LENGTH: 47
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 6
cagcttcctc attgatggtt tctttttaac accatgctaa acacagt                47
```